United States Patent
Davis et al.

(10) Patent No.: US 12,285,435 B2
(45) Date of Patent: Apr. 29, 2025

(54) MULTIVESICULAR LIPOSOME FORMULATIONS OF DEXAMETHASONE

(71) Applicant: Pacira Pharmaceuticals, Inc., San Diego, CA (US)

(72) Inventors: Paige N. Davis, San Diego, CA (US); Soroush M. Ardekani, San Diego, CA (US); Stephanie M. Kurz, San Diego, CA (US); Louie D. Garcia, San Diego, CA (US); Kathleen D. A. Los, San Diego, CA (US); John J. Grigsby, Jr., San Diego, CA (US); Damon A. Leon, San Diego, CA (US); Eran Levy, San Diego, CA (US); Alisha R. Simonian, San Diego, CA (US)

(73) Assignee: Pacira Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 18/046,312

(22) Filed: Oct. 13, 2022

(65) Prior Publication Data

US 2023/0137783 A1    May 4, 2023

Related U.S. Application Data

(60) Provisional application No. 63/255,870, filed on Oct. 14, 2021.

(51) Int. Cl.
*A61K 31/573* (2006.01)
*A61K 9/127* (2006.01)
*A61K 9/1277* (2025.01)

(52) U.S. Cl.
CPC .......... *A61K 31/573* (2013.01); *A61K 9/1277* (2013.01)

(58) Field of Classification Search
CPC ..... A61K 31/573; A61K 9/1277; A61K 9/127
See application file for complete search history.

(56) References Cited

U.S. PATENT DOCUMENTS

| 4,895,719 A | * | 1/1990 | Radhakrishnan ...... A61K 9/008 424/45 |
| 5,766,627 A | | 6/1998 | Mantripragada et al. |

FOREIGN PATENT DOCUMENTS

| CA | 2756 811 | * | 1/2006 |
| WO | 99/13865 | * | 3/1999 |
| WO | WO 19/025319 | | 5/1999 |

OTHER PUBLICATIONS

Dietrich et al., 2015, Particulate versus non-particulate steroids for lumbar transforaminal or interlaminar epidural steroid injections: an update, Skeletal Radiol., 44:149-155.
Donohue et al., 2020, Comparing pain relief and functional improvement between methylprednisolone and dexamethasone lumbosacral transforaminal epidural steroid injections: a self-controlled study, Korean J. Pain, 33(2):192-198.
Ferre et al., 2020, Perineural dexamethasone attenuates liposomal bupivacaine-induced delayed neural inflammation in mice in vivo, British Journal of Anaesthesia, Aug. 2020;125(2):175-183.
Johnson et al., 2021, Dexamethasone, NCBI Bookshelf, https://www.ncbi.nlm.nih.gov/books/NBK482130/?report=printable, 4 pp.
Li et al., 2020, The preparation of dexamethasone sodium phosphate multivesicular liposomes thermosensitive hydrogel and its impact on noise-induced hearing loss in the Guinea pigs, Exp. Cell Res., 387:1-8.
Shapiro, Jun. 11, 2021, Continuous lumbar epidural infusion of steroid, Practical Pain Management, 9(7), 8 pp.
Tsotas et al., 2007, Dexamethasone incorporating liposomes: effect of lipid composition on drug trapping efficiency and vesicle stability, Drug Delivery, 14:441-5445.
Van Boxem et al., 2018, Safe use of epidural corticosteroid injections: recommendations of the WIP Benelux Work Group, Pain Practice, 19(1):61-92.
International Search Report and Written Opinion dated Jan. 5, 2023 in International Application No. PCT/US2022/046535.

* cited by examiner

*Primary Examiner* — Walter E Webb
(74) *Attorney, Agent, or Firm* — Knobbe Martens Olson & Bear LLP

(57) ABSTRACT

Some embodiments of the present application are related to multivesicular liposome (MVL) formulations encapsulating dexamethasone or an ester or an ester salt thereof, for example, dexamethasone sodium phosphate (DSP) that may provide about 3-28 days extended release of dexamethasone. Processes of making and administering dexamethasone encapsulated multivesicular liposome formulations and their uses for treating pain or inflammation are also provided.

22 Claims, 6 Drawing Sheets

MULTIVESICULAR LIPOSOME FORMULATIONS OF DEXAMETHASONE

BACKGROUND

Field

The present disclosure relates to multivesicular liposome (MVL) formulations of dexamethasone or an ester or ester salt thereof, in particular dexamethasone sodium phosphate (DSP), uses thereof and processes of making the same.

Description of the Related Art

Dexamethasone is a synthetic corticosteroid used in the treatment of various conditions, including rheumatic problems, immune diseases, local and systemic inflammatory conditions, skin diseases, severe allergies, asthma, chronic obstructive lung disease, croup, and brain swelling, etc. It is also used to treat symptoms of acute and chronic pain conditions including lumbar radiculopathy. See Donohue, Korean J Pain. 2020; 33(2):192-198. Depending on the indication, pharmaceutical composition containing dexamethasone may be injected via various routes, providing either local (e.g., spinal, epidural, intra-articular) or systemic (e.g., subcutaneous, intramuscular, intravenous) pain management.

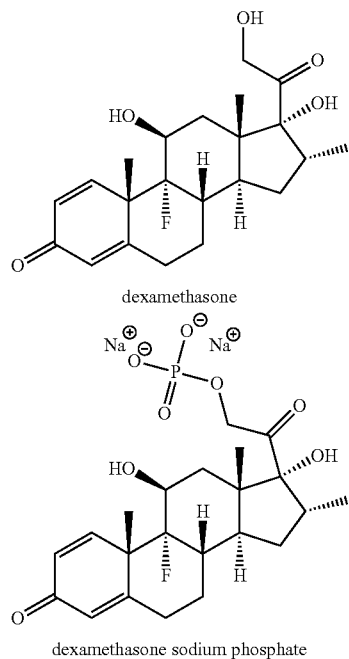

dexamethasone dexamethasone sodium phosphate

Dexamethasone's anti-inflammatory effects act primarily via inhibition of inflammatory cells. For example, DSP, a water-soluble inorganic ester prodrug of dexamethasone, may be formulated as a non-particulate steroid, which may have a safer toxicity profile than particulate steroids. Although DSP provides added benefits to patients with acute or chronic pain conditions, the use of DSP may be limited due to its rapid absorption into the blood stream (plasma half-life ~200 min) compared to particulate steroids. Particulate steroids may have more desirable pharmacokinetic profile to provide extended pain relief, however, it may have serious adverse events when used for spine injections, including blood vessel injury or spasm, or even embolization through vessels causing spinal cord infarction. Certain particulate steroids have significantly higher percentage of large particles and may occlude vessels. Light microscopy studies have demonstrated that the particles in these steroid preparations are either larger than red blood cells or form aggregates larger than red blood cells. See Derby et al., "Size and aggregation of corticosteroids used for epidural injections," Pain Med. 2008; 9:227-34.

Accordingly, there is a need for a stable dexamethasone formulation with prolonged sustained release profile to provide multi-day exposure of efficacious drug levels with concomitant pain relief that are also safer than particulate steroids. The long-acting formulation would allow patients to receive a single injection. The multivesicular liposome formulations described herein address these needs and provide other advantages as described in details below.

SUMMARY

Embodiments of the present application relate to compositions comprising dexamethasone or an ester analog or prodrug thereof, for example, dexamethasone sodium phosphate (DSP) encapsulated multivesicular liposomes, processes of making the same, and uses thereof. Multivesicular liposome formulation of dexamethasone sodium phosphate intended to provide sustained release of dexamethasone sodium phosphate over the span of 7 to 28 days, prolonging the therapeutic effect of the DSP, while minimizing the undesirable side effects of immediate release formulations of dexamethasone sodium phosphate. Processes of making multivesicular liposomes containing DSP are also provided.

Some embodiments of the present disclosure relate to compositions of dexamethasone encapsulated multivesicular liposomes (MVLs), comprising:
  dexamethasone, an ester or an ester salt thereof, encapsulated in a plurality of internal aqueous chambers of the MVLs separated by lipid membranes, wherein the lipid membranes comprise at least one amphipathic lipid and at least one neutral lipid;
  an aqueous medium in which the dexamethasone encapsulated MVLs are suspended;
  wherein the pH of the internal aqueous chambers of the MVLs is about 5.5 to about 8. In some embodiments, the pH of the internal aqueous chambers of the MVLs is about 6.5 to about 7.5. In one embodiment, the pH of the internal aqueous chambers of the MVLs is about 7.5. In some embodiments, the composition also comprises unencapsulated dexamethasone or the ester or ester salt thereof, also known as free dexamethasone or the ester or ester salt thereof. For example, the composition may comprise less than 10%, 9%, 8%, 7%, 6%, 5%, 4%, 3%, 2%, or 1% of free unencapsulated dexamethasone, the ester or ester salt thereof by weight. In some embodiments, the lipid membranes further comprise cholesterol and/or a plant sterol. In some embodiments, the amphipathic lipid comprises a phosphatidylcholine or a salt thereof, a phosphatidylglycerol or a salt thereof, or combinations thereof. In some further embodiments, the phosphatidylglycerol is DPPG. In some further embodiments, the phosphatidylcholine is selected from the group consisting of DEPC, DSPC, DMPC, DOPC, DPPG, and salts and combinations thereof. In some further embodiments, the neutral lipid comprises triglyceride, propylene glycol ester, ethylene glycol ester, or squalene, or combinations thereof. In some further embodiments, the neutral lipid comprises triglyceride. In further embodiments, the triglyceride comprises triolein or tricaprylin, or a combination thereof. In some such embodiments, the percentage of triolein or tricaprylin in the lipid membrane is about 0.5% to about 30% by weight.

In some embodiments of the composition described herein, the concentration of dexamethasone or the ester or ester salt thereof in the composition is from about 1 mg/mL to about 20 mg/mL, from about 2 mg/mL to about 15 mg/mL, from about 3.5 to about 10 mg/mL, from about 6 mg/mL to about 8 mg/mL, or about 7 mg/mL. In some embodiments, the aqueous medium in which the dexamethasone encapsulated MVLs are suspended has a pH range from about 5.5 to about 10. In further embodiments, the aqueous medium has a pH range from about 6.5 to about 7.5, about 6.6 to about 7.2, or about 7.0.

In some embodiments of the composition described herein, the multivesicular liposomes have a $D_{50}$ particle size distribution range from about 1 µm to about 50 µm, from about 1 µm to about 40 µm, from about 10 µm to about 40 µm, from about 15 µm to about 40 µm, or from about 20 µm to about 40 µm.

In some embodiments of the composition described herein, the percent packed particle volume (% PPV) of the dexamethasone encapsulated MVLs in the composition is about 10% to 65%, about 15% to about 45%, about 20% to about 45%, about 18% to about 25%, about 20% to about 40%, about 25% to about 35%, or about 35% to about 45%.

In some embodiments of the composition described herein, the multivesicular liposomes provide sustained release of dexamethasone, or the ester or the ester salt thereof, for 3 to 35 days, or for 14 to 28 days.

In any embodiments of the composition described herein, the dexamethasone or the ester or ester salt thereof is dexamethasone sodium phosphate (DSP).

Some embodiments of the present disclosure relate to a method of treating or ameliorating pain or inflammation in a subject in need thereof, comprising administering a pharmaceutical composition containing multivesicular liposomes encapsulating dexamethasone, or an ester or an ester salt as described herein to the subject. In some embodiments, the administration is selected from the group consisting of subcutaneous injection, tissue injection, intramuscular injection, intraarticular injection, spinal injection, intraocular injection, epidural injection, intrathecal injection, intraotic injection, and perineural injection, and combinations thereof. In further embodiments, administration is spinal injection, epidural injection, or intrathecal injection. In further embodiments, a single administration provides a sustained release of dexamethasone for about 3 days to about 35 days, or for about 7 days to about 28 days. In further embodiments, the Tmax of dexamethasone is from about 1 hour to about 168 hours.

Some embodiments of the present disclosure relate to a process for preparing dexamethasone encapsulated multivesicular liposomes, comprising:
(a) mixing a first aqueous solution comprising dexamethasone, an ester or an ester salt thereof with a lipid solution comprising at least one water-immiscible organic solvent, at least one amphipathic lipid, and at least one neutral lipid to form a first water-in-oil emulsion;
(b) mixing the first water-in-oil emulsion with a second aqueous solution to form a second water-in-oil-in water emulsion; and
(c) substantially removing the water-immiscible organic solvent from the second emulsion to form a first aqueous suspension of dexamethasone encapsulated MVLs. In some embodiments, the lipid solution further comprises dexamethasone or the ester or ester salt thereof. In some embodiments, the process further includes exchanging the aqueous supernatant in the first aqueous suspension with a third aqueous solution one or more times to provide a final aqueous suspension of dexamethasone encapsulated MVLs, wherein the internal pH of the dexamethasone encapsulated MVLs in the final aqueous suspension is from about 5.5 to about 8. In some embodiments, the third aqueous solution is a buffered saline solution. In some embodiments, the pH of the first aqueous solution is from about 5.5 to about 8.0. In further embodiments, the pH of the first aqueous solution is from about 6.5 to about 7.5. In some embodiments, the second aqueous solution comprises at least one pH modifying agent and at least one tonicity agent. In some such embodiments, the tonicity agent comprises sorbitol, sucrose, or dextrose, or combinations thereof. In some embodiments, the pH of the second aqueous solution is from about 6.0 to about 11.5. In further embodiments, the pH of the second aqueous solution is from about 7 to about 10, or from about 9 to about 10, or about 10. In some embodiments, the volume of the lipid solution is greater than the volume of the first aqueous solution. In some embodiments, wherein the mixing in step (b) is performed at a high shear speed from about 500 rpm to about 10,000 rpm, from about 1200 rpm to about 4500 rpm, or from about 2000 rpm to about 9000 rpm.

In some embodiments of the process described herein, the concentration of dexamethasone or the ester or ester salt thereof in the final aqueous suspension is from about 1 mg/mL to about 20 mg/mL, from about 2 mg/mL to about 15 mg/mL, from about 3 mg/mL to about 10 mg/mL, from about 6 mg/mL to about 8 mg/mL, or about 7 mg/mL. In some embodiments, the multivesicular liposomes in the final aqueous suspension have a $D_{50}$ particle size distribution ranging from about 1 µm to about 50 µm, from about 1 µm to about 40 µm, from about 10 µm to about 35 µm, from about 15 µm to about 25 µm, or from about 20 µm to about 40 µm. In some embodiments, the pH of the final aqueous suspension is from about 6.5 to about 7.5, from about 6.6 to about 7.2, from about 7.5 to about 8.5, or about 7.0. In some embodiments, the internal pH of the dexamethasone encapsulated MVLs in the final aqueous suspension is from about 6.5 to about 7.5, or from about 7.1 to about 7.3.

In some embodiments of the process described herein, unencapsulated dexamethasone or the ester or ester salt thereof is about 10%, 9%, 8%, 7%, 6%, 5%, 4%, 3%, 2%, 1% or less by weight of the total amount of dexamethasone or the ester or ester salt thereof in the final aqueous suspension of the dexamethasone MVLs.

In any embodiments of the process described herein, dexamethasone or the ester or ester salt thereof may be in the form of dexamethasone sodium phosphate (DSP).

Further embodiments of the present application relate to a pharmaceutical composition comprising dexamethasone encapsulated multivesicular liposomes prepared by the process described herein. In further embodiments, the pharmaceutical composition may be directly administered to a subject in need thereof without further purification.

DETAILED DESCRIPTION

Figure 1:
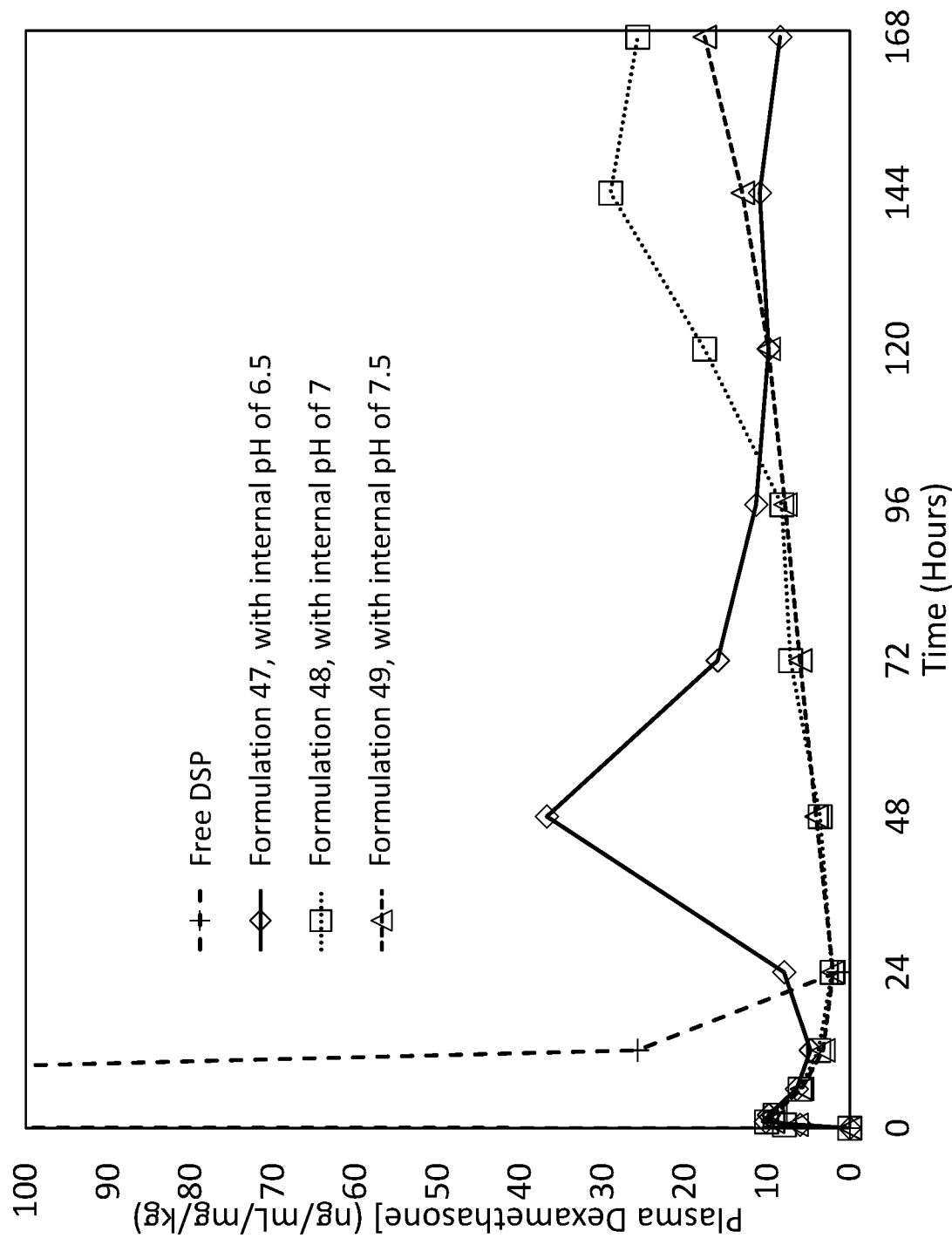
FIG. 1 is a line chart illustrating the dose normalized dexamethasone plasma levels as a function of time, following administration of several dexamethasone sodium phosphate encapsulated multivesicular liposomes (DSP-MVLs) compositions with varying internal pH as compared to dexamethasone sodium phosphate in a saline solution.

The present application provides pharmaceutical compositions comprising multivesicular liposome compositions encapsulating dexamethasone, an ester or an ester salt thereof, in the internal aqueous chambers of the MVLs. In some embodiments, the dexamethasone is dexamethasone sodium phosphate (i.e., DSP-MVLs). A single dose of a multivesicular liposome composition encapsulating dexamethasone sodium phosphate (DSP-MVL) may be administered once every 3 to 35 days or every 7 to 28 days for the treatment of inflammation and pain. This eliminates the need for continuous IV infusions, which are generally restricted to inpatient use, and which can be associated with various complications (blockage, infection, infiltration, phlebitis, inflammation, thrombosis, bruising, hematoma, etc.). The present embodiments also provide the processes of preparing dexamethasone encapsulated MVLs such as DSP-MVLs and the methods of using the DSP-MVL formulations for treating, ameliorating or preventing pain, swelling, heat or redness, comprising administering a pharmaceutical composition comprising dexamethasone encapsulated MVLs such as DSP-MVLs as described herein, to a subject in need thereof.

Definitions

The section headings used herein are for organizational purposes only and are not to be construed as limiting the subject matter described.

As used herein, an ester of dexamethasone may include an ester formed from the reaction of a hydroxy group of dexamethasone with an organic acid or an inorganic acid. For example, dexamethasone phosphate is formed from the reaction of dexamethasone with phosphoric acid.

As used herein, an ester salt of dexamethasone may include an inorganic or organic ester of dexamethasone where the ester is also in a salt form. For example, dexamethasone sodium phosphate is a sodium salt of dexamethasone phosphate.

As used herein, the term "dexamethasone encapsulated multivesicular liposomes", "dexamethasone-MVL" or "dexamethasone-MVLs" refer to a multivesicular liposome composition encapsulating dexamethasone, or an ester or ester salt thereof, as described herein. The term "DSP-MVL" or "DSP-MVLs" refers to a multivesicular liposome composition encapsulating dexamethasone sodium phosphate. Dexamethasone-MVLs or DSP-MVLs may be characterized by a packed particle volume (PPV) measured in % (v/v). In some embodiments, such Dexamethasone-MVLs or DSP-MVLs formulations contain from about 10% to about 80% (v/v), from about 15% to about 75% (v/v), or from about 20% to about 70% (v/v), or from about 30% to about 50% (v/v), or from about 20% to about 40% (v/v), or from about 40% to about 60% (v/v), multivesicular liposome particles. In particular embodiments, Dexamethasone-MVLs or DSP-MVLs formulations contain about 10%, 15%, 18%, 20%, 25%, 30%, 35%, 40%, 45% or 50% (v/v) multivesicular liposome particles, or a range defined by any two of the preceding values.

In some embodiments, the composition is a pharmaceutical formulation, where the dexamethasone sodium phosphate encapsulated multivesicular liposome particles are suspended in a liquid suspending medium to form a suspension. In some such embodiments, the Dexamethasone-MVLs or DSP-MVL suspension may also include free or unencapsulated dexamethasone sodium phosphate. In some cases, the free or unencapsulated dexamethasone sodium phosphate may be less than about 10%, 9%, 8%, 7%, 6%, 5%, 4%, 3%, 2%, 1%, 0.5%, 0.2% or 0.1%, by weight of the total amount of the dexamethasone sodium phosphate in the composition, or in a range defined by any of the two preceding values.

As used herein, the term "encapsulated" means that dexamethasone sodium phosphate is inside a liposomal particle, for example, the MVL particles, the unilamellar vesicles (ULVs) or multilamellar vesicles (MLVs). In some instances, dexamethasone sodium phosphate may also be on an inner surface, or intercalated in a membrane, of the MVLs.

As used herein, the term "unencapsulated dexamethasone sodium phosphate" or "free dexamethasone sodium phosphate" refers to dexamethasone sodium phosphate outside the liposomal particles, for example the MVL, UVL or MLV particles. For example, unencapsulated dexamethasone sodium phosphate may reside in the suspending solution of these particles.

As used herein, the term "median particle diameter" refers to volume weighted median particle diameter of a suspension.

As used herein, a "pH adjusting agent" refers to a compound that is capable of modulating the pH of an aqueous phase.

As used herein, the terms "tonicity" and "osmolality" are measures of the osmotic pressure of two solutions, for example, a test sample and water separated by a semi-permeable membrane. Osmotic pressure is the pressure that must be applied to a solution to prevent the inward flow of water across a semi-permeable membrane. Osmotic pressure and tonicity are influenced only by solutes that cannot readily cross the membrane, as only these exert an osmotic pressure. Solutes able to freely cross the membrane do not affect tonicity because they will become equal concentrations on both sides of the membrane. An osmotic pressure provided herein is as measured on a standard laboratory vapor pressure or freezing point osmometer.

As used herein, the term "sugar" as used herein denotes a monosaccharide or an oligosaccharide. A monosaccharide is a monomeric carbohydrate which is not hydrolysable by acids, including simple sugars and their derivatives, e.g., aminosugars. Examples of monosaccharides include sorbitol, glucose, fructose, galactose, mannose, sorbose, ribose, deoxyribose, dextrose, neuraminic acid. An oligosaccharide is a carbohydrate consisting of more than one monomeric saccharide unit connected via glycosidic bond(s) either branched or in a chain. The monomeric saccharide units within an oligosaccharide can be the same or different. Depending on the number of monomeric saccharide units the oligosaccharide is a di-, tri-, tetra-, penta- and so forth saccharide. In contrast to polysaccharides, the monosaccharides and oligosaccharides are water soluble. Examples of oligosaccharides include sucrose, trehalose, lactose, maltose and raffinose.

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise. As used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. The use of "or" or "and" means "and/or" unless stated otherwise. Furthermore, use of the term "including" as well as other forms, such as "include," "includes," and "included," is not limiting. As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least." When used in the context of a process, the term "comprising" means that the process includes at least the recited steps, but may include additional steps. When used in the context of a compound, composition, or device, the term "comprising" means that the compound, composition, or device includes at least the recited features or components, but may also include additional features or components.

Multivesicular Liposomes Compositions

MVLs are a group of unique forms of synthetic membrane vesicles that are different from other lipid-based delivery systems such as unilamellar liposomes and multilamellar liposomes (Bangham, et al., J Mol. Bio., 13:238-252, 1965). The main structural difference between multivesicular liposomes and unilamellar liposomes (also known as unilamellar vesicles, "ULVs"), is that multivesicular liposomes contain multiple aqueous chambers per particle. The main structural difference between multivesicular liposomes and multilamellar liposomes (also known as multilamellar vesicles, "MLVs"), is that in multivesicular liposomes the multiple aqueous chambers are non-concentric. Multivesicular liposomes generally have between 100 to 1 million chambers per particle and all the internal chambers are interconnected by shared lipid-bilayer walls that separate the chambers. The structural differences between unilamellar, multilamellar, and multivesicular liposomes are illustrated in Sankaram et al., U.S. Pat. Nos. 5,766,627 and 6,132,766.

The structural and functional characteristics of multivesicular liposomes are not directly predictable from current knowledge of unilamellar vesicles and multilamellar vesicles. Multivesicular liposomes have a very distinctive internal morphology, which may arise as a result of the special method employed in the manufacture. Topologically, multivesicular liposomes are defined as having multiple non-concentric chambers within each particle, resembling a "foam-like" or "honeycomb-like" matrix; whereas multilamellar vesicles contain multiple concentric chambers within each liposome particle, resembling the "layers of an onion."

The presence of internal membranes distributed as a network throughout multivesicular liposomes may serve to confer increased mechanical strength to the vesicle. The particles themselves can occupy a very large proportion of the total formulation volume. The packed particle volume (PPV) of MVLs which is measured in a manner analogous to a hematocrit, representing the volume of the formulation that the particles make up and can approach as high as 80%. Typically, the PPV is about 50%. At 50% PPV, the multivesicular liposome formulation typically consists of less than 5% w/w lipid. Thus, the encapsulated volume is approximately 50% while having a relatively low lipid concentration. The multivesicular nature of multivesicular liposomes also indicates that, unlike for unilamellar vesicles, a single breach in the external membrane of multivesicular vesicles will not result in total release of the internal aqueous contents.

Thus, multivesicular liposomes formulations consist of microscopic, spherical particles composed of numerous non-concentric aqueous chambers. The individual chambers are separated by lipid bilayer membranes composed of synthetic versions of naturally occurring lipids, resulting in a delivery vehicle that is both biocompatible and biodegradable. Thus, dexamethasone-MVL formulations include microscopic, spherical particles composed of numerous nonconcentric aqueous chambers encapsulating dexamethasone for controlled release drug delivery. Such formulation is intended to prolong the local delivery of dexamethasone sodium phosphate, thereby enhancing the duration of action of the reduction of inflammation or pain. The dexamethasone-MVL composition provides either local site or systemic sustained delivery, and can be administered by a number of routes including subcutaneous injection, intra-articular injection, intramuscular injection, intraperitoneal injection, intrathecal injection, tissue injection, spinal injection, intraocular injection, epidural injection, intraotic injection, perineural injection, or infiltration to an open wound, or body cavities such as the nasal cavity, and combinations thereof.

In some embodiments, the MVLs may optionally encapsulate or comprise additional therapeutic agent(s). In some other embodiments, dexamethasone or an ester or an ester salt thereof (e.g., DSP) is the only therapeutic agent in the MVLs.

Some embodiments of the present application relate to a composition of dexamethasone encapsulated multivesicular liposomes (MVLs), comprising:

dexamethasone, an ester or an ester salt thereof, encapsulated in a plurality of internal aqueous chambers of the MVLs separated by lipid membranes, wherein the lipid membranes comprise at least one amphipathic lipid and at least one neutral lipid;

an aqueous medium in which the dexamethasone encapsulated MVLs are suspended; wherein the pH of the internal aqueous chambers of the MVLs is about 5.5 to about 8.

In some embodiments, the composition also comprises unencapsulated dexamethasone or the ester or ester salt thereof, also known as free dexamethasone. For example, the composition may comprise less than 10%, 9%, 8%, 7%, 6%, 5%, 4%, 3%, 2%, or 1% of free unencapsulated dexamethasone or the ester or ester salt thereof by weight.

In some further embodiments, such pharmaceutical composition is for a single injection or administration (i.e., a single dose). A single administration of the pharmaceutical composition may provide sustained release of dexamethasone sodium phosphate for 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 days, or a range defined by any two of the preceding values. For example, a single administration of the DSP-MVLs may provide a sustain release of DSP for 3 to 35 days, or 7 to 28 days. One skilled in the art understand the sustained release duration of dexamethasone, or the ester or ester salt thereof may depend on the route of administration. For example, the sustained release duration for subcutaneous injection or infusion may be from about 14 days to 28 days; while epidural injection may have a shorter sustained release profile (e.g., 3 to 5 days or 3 to 7 days) possibly due to the large volume of the injection space and the frequency of the turnover of the fluid within the injection space, without being bound by a particular theory. In some embodiments, the $T_{max}$ of dexamethasone sodium phosphate from a single administration of the pharmaceutical composition is from about 1 hour to about 264 hour or from about 1 hours to about 168 hours, for example, about 1, 6, 12, 18, 24, 30, 36, 42, 48, 54, 60, 66, 72, 78, 84, 90, 96, 102, 108, 114, 120, 126, 132, 138, 144, 148, 152, 156, 160, 154, or 168, 172, 176, 180, 184, 188, 192, 196, 200, 204, 208, 212, 216, 220, 224, 228, 232, 236, 240, 244, 248, 252, 256, 260, or 264 hours. The lower Tmax value may be contributed by the free dexamethasone or the ester or ester salt thereof present in the composition. The encapsulated dexamethasone or the ester or ester salt (such as DPS) starts to release from the MVL particles starting from about 18 to 24 hour time point.

pH Modifying Agents

In some embodiments, the internal aqueous chambers of the MVLs comprises one or more pH modifying agents to modulate the release rate of the dexamethasone. The pH modifying agents that may be used in the present MVL formulations are selected from organic acids, organic bases, inorganic acids, or inorganic bases, or combinations thereof. Suitable inorganic acids (also known as mineral acids) that can be used in the present application include, but are not limited to hydrochloric acid (HCl), sulfuric acid ($H_2SO_4$), phosphoric acid ($H_3PO_4$), nitric acid ($HNO_3$), etc. Suitable organic acids that can be used in the present application include, but are not limited to acetic acid, aspartic acid, citric acid, formic acid, glutamic acid, glucuronic acid, lactic acid, malic acid, tartaric acid, etc. Suitable organic bases that can be used in the present application include, but are not limited to histidine, arginine, lysine, tromethamine (Tris), etc. Suitable inorganic bases that can be used in the present application include, but are not limited to sodium hydroxide, calcium hydroxide, magnesium hydroxide, potassium hydroxide, etc.

In some embodiments, the pH modifying agents are selected from the group consisting of inorganic acids, organic bases, and combinations thereof. In some embodiments, the pH modifying agents are selected from the group consisting of organic acids, organic bases, and combinations thereof. In some embodiments, the inorganic acid is phosphoric acid. In some embodiments, the organic acid is selected from tartaric acid, or glutamic acid, or a combination thereof. In some embodiments, the organic base is selected from histidine, or lysine, or combinations thereof. In some further embodiments, at least one pH modifying agent resides in the first aqueous solution of the multivesicular liposomes and said pH modifying agent comprises an inorganic acid, for example, phosphoric acid. In further embodiments, at least one pH modifying agent resides in a second aqueous solution used in the process of preparing the multivesicular liposomes, and said pH modifying agent comprises an organic base. In further embodiments the organic base comprises histidine, lysine, or a combination thereof.

In some embodiments, the internal pH of the MVLs is about 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9 or 8.0, or within a range defined by any two of the preceding pH values. In some further embodiments, the pH of the internal aqueous chambers of the MVLs is about 6.5 to about 7.5, or from about 7.1 to about 7.3. In one embodiment, the pH of the internal aqueous chambers of the MVLs is about 7.5. It has been observed that the internal pH of the MVLs play an important role in modulating the sustained release rate of dexamethasone. For example, DSP-MVL formulations made with a pH 6.5 first aqueous solution had a $T_{max}$ at 48 hours, while DSP-MVL formulations made with a pH 7 first aqueous solution had a $T_{max}$ at 144 hours. DSP-MVL formulations made with a pH 7.5 first aqueous solution had a $T_{max}$ at 168 hours, and appeared to be continuing to release and would reach its $T_{max}$ after 168 hours. See FIG. 1. In addition, the internal pH of the dexamethasone is important for the overall stability of the dexamethasone encapsulated MVL particles. It has been observed that when the pH of the first aqueous solution increased from about 6.5 to about 7.5, the amount of unencapsulated DSP in the supernatant compared to the total amount of DSP substantially decreased, for example, from about 5% to about 1.5% in a stability testing conducted at 30° C. See FIG. 2.

In some embodiments of the composition described herein, the MVL particles are suspended in an aqueous solution (i.e., a suspending solution). The suspending solution may comprise one or more pH modifying agents, and/or may perform a buffering function. The suspending solution defines the external pH of the MVL formulation. In some embodiments, the pH of the suspending solution is about 5.5, 6.0, 6.5, 7.0, 7.5, 8.0, 8.5, 9.0, 9.5 or 10, or within a range defined by any two of the preceding pH values. In some embodiments, the dexamethasone sodium phosphate encapsulated MVLs composition has an external pH (i.e., the pH of the suspending solution where multivesicular liposome particles reside) from about 5.5 to about 10, about 6.0 to about 9.5, from about 6.5 to about 9, from 7.0 to about 8.5, from about 6.5 to about 7.5, from about 6.6 to about 7.2, or about 7.0.

Lipid Components

In some embodiments of the composition described herein, the lipid components of the MVLs comprise at least one amphipathic lipid and at least one neutral lipid.

A "water-in-oil" type emulsion is formed from two immiscible phases, a lipid phase and a first aqueous phase. The lipid phase is made up of at least one amphipathic lipid and at least one neutral lipid in a volatile organic solvent, and optionally cholesterol and/or cholesterol derivatives. The term "amphipathic lipid" refers to molecules having a hydrophilic "head" group and a hydrophobic "tail" group and may have membrane-forming capability. As used herein, amphipathic lipids include those having a net negative charge, a net positive charge, and zwitterionic lipids (having no net charge at their isoelectric point). The term "neutral lipid" refers to oils or fats that have no vesicle-forming capabilities by themselves, and lack a charged or hydrophilic "head" group. Examples of neutral lipids include, but are not limited to, glycerol esters, glycol esters, tocopherol esters, sterol esters which lack a charged or hydrophilic "head" group, and alkanes and squalenes.

The amphipathic lipid is chosen from a wide range of lipids having a hydrophobic region and a hydrophilic region in the same molecule. Suitable amphipathic lipids include, but are not limited to zwitterionic phospholipids, including phosphatidylcholines, phosphatidylethanolamines, sphingomyelins, lysophosphatidylcholines, and lysophosphatidylethanolamines; anionic amphipathic phospholipids such as phosphatidylglycerols, phosphatidylserines, phosphatidylinositols, phosphatidic acids, and cardiolipins; cationic amphipathic lipids such as acyl trimethylammonium propanes, diacyl dimethylammonium propanes, stearylamine, and the like. Non-limiting exemplary phosphatidyl cholines include dioleyl phosphatidyl choline (DOPC), dierucoyl phosphatidyl choline or 1,2-dierucoyl-sn-glycero phosphocholine (DEPC), 1,2-didecanoyl-sn-glycero-3-phosphocholine (DDPC), 1,2-dilinoleoyl-sn-glycero-3-phosphocholine (DLOPC), 1,2-dilauroyl-sn-glycero-3-phosphocholine (DLPC), 1,2-dimyristoyl-sn-glycero-3-phosphocholine (DMPC), 1,2-dipalmitoyl-sn-glycero-3-phosphocholine (DPPC), 1,2-distearoyl-sn-glycero-3-phosphocholine (DSPC), 1-myristoyl-2-palmitoyl-sn-glycero 3-phosphocholine (MPPC), 1-myristoyl-2-stearoyl-sn-glycero-3-phosphocholine (MSPC), 1-palmitoyl-2-myristoyl-sn-glycero-3-phosphocholine (PMPC), 1-palmitoyl-2-oleoyl-sn-glycero-3-phosphocholine (POPC), 1-palmitoyl-2-stearoyl-sn-glycero-3-phosphocholine (PSPC), 1-stearoyl-2-myristoyl-sn-glycero-3-phosphocholine (SMPC), 1-stearoyl-2-oleoyl-sn-glycero-3-phosphocholine (SOPC), or 1-stearoyl-2-palmitoyl-sn-glycero-3-phosphocholine (SPPC). Non-limiting examples of phosphatidyl glycerols include dipalmitoylphosphatidylglycerol or 1,2-dipalmitoyl-sn-glycero-3-phospho-rac-(1-glycerol) (DPPG), 1,2-dierucoyl-sn-glycero-3-phospho-rac-(1-glycerol) (DEPG), 1,2-dilauroyl-sn-glycero-3-phospho-rac-(1-glycerol) (DLPG), 1,2-dimyristoyl-sn-glycero-3-phospho-rac-(1-glycerol) (DMPG), 1,2-dioleoyl-sn-glycero-3-phospho-rac-(1-glycerol) (DOPG), 1,2-distearoyl-sn-glycero-3-phospho-rac-(1-glycerol) (DSPG), 1-palmitoyl-2-oleoyl-sn-glycero-3-phospho-rac-(1-glycerol) (POPG), or salts thereof, for example, the corresponding sodium salts, ammonium salts, or combinations of the salts thereof.

Suitable neutral lipids include but are not limited to triglycerides, propylene glycol esters, ethylene glycol esters, and squalene. Non-limiting exemplary triglycerides useful in the instant formulations and processes are triolein (TO), tripalmitolein, trimyristolein, trilinolein, tributyrin, tricaproin, tricaprylin (TC), and tricaprin. The fatty chains in the triglycerides useful in the present application can be all the same, or not all the same (mixed chain triglycerides), or all different. Propylene glycol esters can be mixed diesters of caprylic and capric acids.

In some embodiments of the composition described herein, the lipid components contain phosphatidyl choline or salts thereof, phosphatidyl glycerol or salts thereof, and at least one triglyceride. In some embodiments, the phosphatidyl choline is dierucoyl phosphatidyl choline (DEPC). In some embodiments, the phosphatidyl glycerol is dipalmitoyl phosphatidyl glycerol (DPPG) or a salt thereof, such as sodium salt of DPPG. In some embodiments, the phosphatidylcholine is selected from DEPC, DSPC, DMPC, DOPC, or a combination thereof. In further embodiments, the DEPC and the DPPG (or a salt thereof) are present in MVLs in a mass ratio of DEPC:DPPG of about 10:1 to about 1:1, or about 10:1 to about 3:1. In some embodiments, the DEPC and the DPPG (or a salt thereof) are present in MVLs in a mass ratio of DEPC:DPPG of about 7:1, 6:1, 5:1, 4:1, or 3:1.

In further embodiments, the neutral lipid comprises triglyceride, propylene glycol ester, ethylene glycol ester, or squalene, or combinations thereof. In some embodiments, the neutral lipid comprises triglyceride. In some embodiments the triglyceride comprises triolein or tricaprylin, or a combination thereof. In some further embodiments, the multivesicular liposomes further comprise cholesterol and/or a plant sterol.

It has been observed that lowering the amount of tricaprylin while keeping other lipids constant resulted in an increased API:PPV ratio, and results in increased encapsulation efficiency. See FIG. 3. For example, decreasing the tricaprylin concentration in the lipid solution from about 14 mg/mL to about 11 mg/mL increased the encapsulation efficiency from 0.13 to 0.16 ([DSP]/% PPV). Surprisingly, decreasing the tricaprylin concentration in the lipid solution to about 8.5 mg/mL increased the encapsulation efficiency to 0.19 ([DSP]/% PPV).

It was also observed that the addition of triolein (TO) to the lipid components increased the pharmacokinetic release profile of DSP. For example, in one embodiment, adding an additional 2% triolein (2% relative to the molar concentration of tricaprylin) in the lipid components increased the pharmacokinetic release profile of DSP from about 2 weeks to about 4 weeks. See FIG. 4. Furthermore, it was also observed the addition of triolein to the lipid components does not affect product stability at 37° C. In some embodiments, the percentage of triolein, relative to the lipid components, in the lipid membrane (or in the MVLs) is from about 0.5% to about 20%, from about 1% to about 15%, from about 2% to about 10%, from about 0.1% to about 2%, or from about 10% to about 15%. For example, in some embodiments, 2% to 10% triolein relative to the amount of tricaprylin may be added to the lipid solution.

In addition, it was also observed that DSP-MVL formulations utilizing higher lipid component concentrations of DEPC, DPPG, cholesterol, and tricaprylin (e.g., Lipid Formulation 2) result in higher yields and lower % PPV when compared to DSP-MVL formulations utilizing lower lipid component concentrations of DEPC, DPPG, cholesterol, and tricaprylin (e.g., Lipid Formulation 1).

Tonicity Agents

In some embodiments of the composition described herein, the internal aqueous chambers of the MVLs further comprises one or more tonicity agents. Tonicity agents sometimes are also called osmotic agents. Non-limiting exemplary osmotic agents suitable for the MVL formulation of the present application include monosaccharides (e.g., glucose, and the like), disaccharides (e.g., sucrose and the like), polysaccharide or polyols (e.g., sorbitol, mannitol, Dextran, and the like), or amino acids.

In some embodiments, the one or more tonicity agents may be selected from an amino acid, a sugar, or combinations thereof. In some further embodiments, one or more tonicity agents are selected from dextrose, sorbitol, sucrose, lysine, or combinations thereof.

Particle Sizes

In some embodiments of the composition described herein, the dexamethasone or an ester of ester salt thereof (e.g., DSP) encapsulated MVL particles have a median particle diameter of about 5, 10, 15, 20, 25, 30, 35, 40, 45, 50, 55, 60, 65, 70, 75, 80, 85, 90, 95, or 100 μm, or within a range defined by any two of the preceding values. In some further embodiments, the multivesicular liposomes have a median particle diameter ($D_{50}$) ranging from about 1 μm to about 50 μm, from about 15 μm to about 40 μm, from about 20 μm to about 40 μm. In still some further embodiments, the multivesicular liposomes have a median particle diameter of about 15 μm, 20 μm, 25 μm, 30 μm, 35 μm or 40 μm.

In some embodiments, the MVL particles are suspended in a liquid suspending solution or medium. In some further embodiments, the liquid suspending medium is a buffered saline solution. In some such embodiments, the MVL particle suspension has a PPV (%) of about 10%, 15%, 20%, 25%, 30%, 35%, 40%, 45%, 50%, 55%, 60%, or 65%. In some embodiments, the % PPV is from about 18% to about 25%. In other embodiments, the % PPV is from about 35% to about 45%. In further embodiments, the concentration of dexamethasone or an ester or an ester sal thereof in the composition is about 1.0 mg/mL, 1.5 mg/mL, 2.0 mg/mL, 2.5 mg/mL, 3.5 mg/mL, 4.0 mg/mL, 4.5 mg/mL, 5.0 mg/mL, 5.5 mg/mL, 6.0 mg/mL, 6.5 mg/mL, 7.0 mg/mL, 7.5 mg/mL, 8.0 mg/mL, 8.5 mg/mL, 9.0 mg/mL, 9.5 mg/mL, 10 mg/mL, 11 mg/mL, 12 mg/mL, 13 mg/mL, 14 mg/mL, 15 mg/mL, 16 mg/mL, 17 mg/mL, 18 mg/mL, 19 mg/mL, 20 mg/mL, 25 mg/mL, or 30 mg/mL, or in a range defined by any of the two preceding values. In some further embodiments, the concentration of dexamethasone or the ester or ester salt thereof in the composition is from about is from about 1 mg/mL to about 20 mg/mL, from about 2 mg/mL to about 15 mg/mL, from about 3.5 mg/mL to about 10 mg/mL, from about 6 mg/mL to about 8 mg/mL, or about 7 mg/mL.

In any embodiments of the dexamethasone multivesicular liposome compositions described herein, the multivesicular liposomes are stable at 37° C. for at least 2, 3, 4, 5, 6, or 7 days. Furthermore, the formulation may be stable at 5° C. for at least 1 week, 2 weeks, 3 weeks, 4 weeks, 2 months, 3 months, 6 months, 9 months, 12 months, 18 months or 24 months. As used herein, the term "stable" means that the multivesicular liposomes particles in the suspending solution maintain the structural integrity and dexamethasone sodium phosphate remains encapsulated in the multivesicular liposomes without excessively leaking out of multivesicular liposome in free form, during certain storage condition for a period of time. In some embodiments, the dexamethasone encapsulated MVLs (e.g., DSP-MVL) formulations described herein are stable at 5° C. for 6 months with less than about 10%, 9.5%, 9%, 8.5%, 8%, 7.5%, 7%, 6.5%, 6%, 5.5%, 5%, 4.5%, 4%, 3.5%, 3%, 2.5%, 2%, 1.5%, 1%, 0.5%, or 0.1% of dexamethasone by weight in the free or unencapsulated form. In some embodiments, the dexamethasone encapsulated MVLs (e.g., DSP-MVL) formulations described herein are stable at 37° C. for 3 days with less than about 30%, 25%, 20%, 15%, 10%, 9%, 8%, 7%, 6%, 5%, 4%, 3%, 2%, or 1% of DSP by weight in the free or unencapsulated form. In some embodiments, the DSP-MVL formulation contains less than 5% or 4% of free DSP by weight. In some embodiments, the DSP-MVL formulation contains less than 8% or 7% of free DSP by weight after storing at 5° C. for at least 6 months. In some embodiments, it is desirable to have a small amount of free dexamethasone or the ester or ester salt thereof (e.g., DSP) to provide immediate release of the symptoms while the encapsulated dexamethasone or the ester or ester salt thereof provide a long sustained release profile.

In any embodiments of the composition described herein, dexamethasone or the ester or ester salt thereof may be in an ester salt form as dexamethasone sodium phosphate (DSP).

Methods of Treatment

Some embodiments of the present application are related to methods for treating or ameliorating pain, inflammation, nausea, swelling, heat, redness and/or cancer, comprising administering a dexamethasone-MVL (e.g., DSP-MVL) pharmaceutical composition as described herein, to a subject in need thereof. The instant dexamethasone-MVL compositions can be used to treat certain forms of arthritis; skin, blood, kidney, eye, thyroid, and intestinal disorders. For example, the instant dexamethasone-MVL formulations can be used to treat rheumatoid arthritis and other rheumatic diseases, including ankylosing spondylitis, psoriatic arthritis, juvenile rheumatoid arthritis, lupus, and acute gouty arthritis; atopic dermatitis (eczema), psoriasis, pemphigus, severe erythema multiforme (Stevens-Johnson syndrome), exfoliative dermatitis, bullous dermatitis herpetiformis, severe seborrheic dermatitis, severe psoriasis, or mycosis fungoides; ulcerative colitis; multiple sclerosis or myasthenia gravis; leukemias and lymphomas; severe allergies; asthma and breathing disorders.

In some embodiments of the methods described herein, the administration is parenteral. In some further embodiments, the parenteral administration may be selected from the group consisting of subcutaneous injection, tissue injection, intramuscular injection, intraarticular injection, spinal injection, intraocular injection, epidural injection, intrathecal injection, intraotic injection, perineural injection, and combinations thereof. In particular embodiments, the parenteral administration is spinal injection, epidural injection, or intrathecal injection.

In some other embodiments of the method described herein, the pharmaceutical compositions can be administered by bolus injection, e.g., subcutaneous bolus injection, intramuscular bolus injection, intradermal bolus injection and the like. In still other embodiments, the pharmaceutical compositions can be administered by infiltration.

Administration of the instant dexamethasone-MVL formulations is accomplished using standard methods and devices, e.g., pens, injector systems, needle and syringe, a subcutaneous injection port delivery system, catheters, and the like.

In some embodiments, the dexamethasone-MVL pharmaceutical composition may be administered every 7 to 28 days. The number of administrations may change depending on effectiveness of the dose, observed side effects, desire to titrate up to a desired dose, external factors (e.g., a change in another medication), or the length of time that the dosage form has been administered.

In some embodiments, the dexamethasone-MVL pharmaceutical composition is administered in a dose ranging from about 0.1 mg/kg to about 10 mg/kg, from about 0.1 mg/kg to about 5 mg/kg, from about 5 mg/kg to about 10 mg/kg, or from about 0.5 mg/kg to about 2.5 mg/kg. In some embodiments, the DSP-MVL pharmaceutical composition described herein comprise of less than about 25%, 20%, 15%, 10%, 9%, 8%, 7%, 6%, 5%, 4%, 3%, 2%, or 1% of dexamethasone by weight in the free or unencapsulated form.

In some embodiments, a single dose of the DSP-MVL pharmaceutical composition comprises about 0.5 mg/mL, 1.0 mg/mL, 1.5 mg/mL, 2.0 mg/mL, 2.5 mg/mL, 3.5 mg/mL, 4.0 mg/mL, 4.5 mg/mL, 5.0 mg/mL, 5.5 mg/mL, 6.0 mg/mL, 6.5 mg/mL, 7.0 mg/mL, 7.5 mg/mL, 8.0 mg/mL, 8.5 mg/mL, 9.0 mg/mL, 9.5 mg/mL, 10 mg/mL, 15 mg/mL, or 20 mg/mL of dexamethasone. In one embodiment, a single dose of the dexamethasone-MVL pharmaceutical composition comprises about 7 mg/mL of dexamethasone.

In any embodiments of the composition described herein, dexamethasone may be in an ester salt form as dexamethasone sodium phosphate (DSP).

Methods of Manufacturing

Some embodiments of the present application relate to a process for a process for preparing dexamethasone encapsulated multivesicular liposomes, comprising:

(a) mixing a first aqueous solution comprising dexamethasone, an ester or an ester salt thereof with a lipid solution comprising at least one water-immiscible organic solvent, at least one amphipathic lipid, and at least one neutral lipid to form a first water-in-oil emulsion;

(b) mixing the first water-in-oil emulsion with a second aqueous solution to form a second water-in-oil-in water emulsion; and (c) substantially removing the water-immiscible organic solvent from the second emulsion to form a first aqueous suspension of dexamethasone encapsulated MVLs. In some embodiments, the process further includes exchanging the aqueous supernatant in the first aqueous suspension with a third aqueous solution by diafiltration or centrifugation one or more times to provide a final aqueous suspension of dexamethasone encapsulated MVLs.

In some embodiments of the process described herein, the lipid solution further comprises dexamethasone or the ester or ester salt thereof. In some embodiments, the process further comprises exchanging the aqueous supernatant in the first aqueous suspension with a third aqueous solution (e.g., through microfiltration, tangential flow filtration, and/or diafiltration) one or more times to provide a final aqueous suspension of dexamethasone encapsulated MVLs, wherein the internal pH of the dexamethasone encapsulated MVLs in the final aqueous suspension is from about 5.5 to about 8. In some embodiments, the process further includes isolating the multivesicular liposome particles and suspending them in a liquid suspending medium (e.g., a buffered saline solution) to form a suspension of multivesicular liposomes. The final aqueous suspension of dexamethasone encapsulated MVLs may be directly administered to a subject in need thereof without further purification. One or each step of the process described herein may be carried out in an aseptic condition.

In some embodiments of the process described herein, the organic solvent is substantially removed by exposing the second emulsion to a gas atmosphere. Organic solvent may be removed by blowing a gas over the second emulsion, or sparging gas in the second emulsion, or spraying the second emulsion into a chamber with a continuous stream of circulating gas.

In some embodiments of the process described herein, the first aqueous solution comprises dexamethasone, an ester or an ester salt thereof, and at least one pH modifying agent. In some embodiments, the pH modifying agent of the first aqueous solution is an inorganic acid, an organic acid, an inorganic base, or an organic base, or combinations thereof. In some such embodiments, the pH modifying agent is phosphoric acid. In some other embodiments, the pH modifying agent is selected from histidine or lysine. In some embodiments, the first aqueous solution may also include one or more osmotic agents. The osmotic agent may be selected from a saccharide, such as sucrose. In some such embodiments, the volume of the lipid solution is greater than the volume of the first aqueous solution. In some other embodiments of the process described herein, dexamethasone or the ester or ester salt thereof is incorporated into the lipid solution. In some such embodiments, the volume of the lipid solution is the same or substantially the same as the volume of the first aqueous solution. In some other embodiments of the process described herein, the volume of the lipid solution is greater than the volume of the first aqueous solution. Additionally, dexamethasone or the ester or ester salt thereof is incorporated into both the lipid solution and the first aqueous solution.

In some embodiments, the mixing of the first water-in-oil emulsion with a second aqueous solution is performed at a high shear speed from about 500 rpm to about 10,000 rpm. In some embodiments, the mixing of the first water-in-oil emulsion with a second aqueous solution is performed at a high shear speed of about 1,000 rpm, about 1250 rpm, about 1500 rpm, about 1750 rpm, about 2,000 rpm, about 2250 rpm, about 2500 rpm, about 2750 rpm, about 3,000 rpm, about 3250 rpm, about 3500 rpm, about 3750 rpm, about 4,000 rpm, about 4500 rpm, about 5,000 rpm, about 5500 rpm, about 6,000 rpm, about 6500 rpm, about 7,000 rpm, about 7500 rpm, about 8,000 rpm, about 8500 rpm, about 9,000 rpm, about 9500 rpm, or about 10,000 rpm. For example, the mixing of the first water-in-oil emulsion with a second aqueous solution may be performed at a high shear speed of about 8,000 rpm for about five minutes.

In some embodiments of the process described herein, the pH range of the first aqueous solution is about 1.0, 1.5, 2.0, 2.5, 3.0, 3.5, 4.0, 4.5, 5.0, 5.5, 6.0, 6.5, 7.0, 7.5, 8.0, 8.5 or 9.0, or a range defined by any two of proceeding values. In some further embodiments, the pH range of the first aqueous solution is from about 5.5 to about 9.0, from about 6.5 to about 8, or about 7.5. In certain cases, aggregation in the final product was observed when the pH of the first aqueous solution was increased. Surprisingly, the use of histidine as a second aqueous solution pH modifier resulted in extremely aggregated particles after solvent removal. In some embodiments of the process described herein, the pH range of the final aqueous suspension is about 1.0, 1.5, 2.0, 2.5, 3.0, 3.5, 4.0, 4.5, 5.0, 5.5, 6.0, 6.5, 7.0 7.5, 8.0, 8.5 or 9.0, or a range defined by any two of proceeding values. In some further embodiments, the pH range of the final aqueous suspension is from about 5.5 to about 9.0, from about 6.5 to about 7.5, or about 7.0. In some embodiments of the process described herein, the internal pH of the dexamethasone encapsulated MVLs in the final aqueous suspension is from about 5.5 to about 8, for example, the internal pH of the MVLs is about 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9 or 8.0, or within a range defined by any two of the preceding pH values. In further embodiments, the internal pH of dexamethasone encapsulated MVLs in the final aqueous suspension is from about 6.5 to about 7.5, from about 7.1 to about 7.3, or about 7.5.

As described herein, the internal pH of the final dexamethasone MVLs is important for the sustained release profile of the dexamethasone. During the manufacturing process, the internal pH of the final product may be controlled by the pH of first aqueous solution, where dexamethasone is mixed with one or more pH adjusting agents. In one embodiment, the pH adjusting or modifying agent comprises or is an inorganic acid (e.g., phosphoric acid). As described herein, it has been observed that the pH of the first aqueous solution plays an important role during the manufacturing process of dexamethasone-MVLs. For example, in one embodiment, the amount of unencapsulated dexamethasone in the supernatant was reduced in formulations which the pH of the first aqueous solution was about 7.5, compared to formulations which the pH of the first aqueous solution was 6.5 or 7.0. Surprisingly, in formulations which the pH of the first aqueous solution was about 7.5 also prolonged the $T_{max}$ of the dexamethasone plasma levels obtained in rats.

In some embodiments of the process described herein, the osmolality of the first aqueous solution of the MVLs is about 260, 270, 280, 290, 295, 300, 310, 320, 330, 340, or 350 mOsm/kg, or within a range defined by any two of the preceding values. In some further embodiments, the osmolality of the first aqueous solution of the MVLs is from about 250 mOsm/kg to about 350 mOsm/kg, from 260 mOsm/kg to about 330 mOsm/kg, from about 280 mOsm/kg to about 310 mOsm/kg, or about 290 mOsm/kg.

In some embodiments of the process described herein, the second aqueous solution comprises at least one pH modifying agent and at least one tonicity agent. In some such embodiments, the tonicity agent comprises sorbitol, sucrose, or dextrose, or combinations thereof. In some embodiments, the osmolality of the second aqueous solution is about 80, 90, 100, 110, 120, 130, 140, 150, 160, 170, 180, 190, 200, 210, 220, 230, 240, 250, 260, 265, 270, 275, 280, 290, 300, 350, 400, 450, or 500 mOsm/kg, or in a range defined by any two of the preceding values. In some embodiments, the osmolality of the second aqueous solution is from about 150 mOsm/kg to about 300 mOsm/kg, from about 160 mOsm/kg to about 280 mOsm/kg, or from about 200 mOsm/kg to about 275 mOsm/kg. In one embodiment, the osmolality of the second aqueous solution is about 170 mOsm/kg. In one embodiment, the osmolality of the second aqueous solution is about 265 mOsm/kg. In one embodiment, the osmolality of the second aqueous solution is about 270 mOsm/kg. In one embodiment, the osmolality of the second aqueous solution is about 275 mOsm/kg.

In some embodiments of the process described herein, the pH range of the second aqueous solution is about 5.0, 5.5, 6.0, 6.5, 7.0, 7.5, 8.0, 8.5, 9.0, 9.5, 10, 10.5, 11, 11.5, or 12 or in a range defined by any two of the preceding values. In some such embodiments, the pH range of the second aqueous solution is from about 6.0 to about 11.5, or from about 7.0 to about 11, or from about 9.0 to about 10, or about 10.

After the organic solvent is removed, the resulting multivesicular liposome particles are diluted, centrifuged or filtered (e.g., through microfiltration, tangential flow filtration or diafiltration) and the supernatant is replaced with saline, optionally containing one or more buffering agents (e.g., 20 mM sodium phosphate at pH from 5.5 to 7.6, or for example at pH 6.8 or 7). After washing, the MVL particles were diluted in saline or other buffer solutions to yield the final product as a liquid suspension with about 20% to about 45% packed particle volume (PPV). In some such embodiments, the concentration of encapsulated dexamethasone or the ester or ester salt thereof in the suspension is from about 1 mg/mL to about 20 mg/mL, from about 0.2 mg/mL to about 10 mg/mL, from about 0.5 mg/mL to about 9 mg/mL, from about 1 mg/mL to about 8 mg/mL, from about 2 mg/mL to about 6 mg/mL, from about 3 mg/mL to about 5 mg/mL, or from about 6 mg/mL to about 8 mg/mL. In some such embodiments, the unencapsulated or free dexamethasone or the ester or ester salt thereof is about 10%, 9%, 8%, 7%, 6%, 5%, 4%, 3%, 2% or less by weight of total amount of dexamethasone or the ester or ester salt thereof in the suspension. In some embodiments, the concentration of unencapsulated dexamethasone or the ester/ester salt thereof in the final product suspension is less than about 1 mg/mL, 0.9 mg/mL, 0.8 mg/mL, 0.7 mg/mL, 0.6 mg/mL, 0.5 mg/mL, 0.4 mg/mL, 0.3 mg/mL, 0.2 mg/mL, 0.1 mg/mL, 0.05 mg/mL or 0.01 mg/mL.

In some embodiments of the process described herein, the dexamethasone encapsulated MVL particles have a median particle diameter ($d_{50}$) of about 5, 10, 15, 20, 25, 30, 35, 40, 45, 50, 55, 60, 65, 70, 75, 80, 85, 90, 95, or 100 µm, or within a range defined by any two of the preceding values. In some embodiments of the process described herein, the multivesicular liposomes have a $d_{50}$ ranging from about 1 µm to about 50 µm, from about 10 µm to about 45 µm, or from about 20 µm to about 40 µm. In some further embodiments of the process described herein, the multivesicular liposomes have a median particle diameter of about 15 µm, 20 µm, 25 µm, 30 µm or 35 µm, or 40 µm.

Some further embodiments of the present disclosure include dexamethasone encapsulated multivesicular liposomes prepared by the process described herein.

In some embodiments of the process described herein, the lipid components contain phosphatidyl choline or salts thereof, phosphatidyl glycerol or salts thereof, and at least one triglyceride. In some embodiments, the amphipathic lipid comprises phosphatidylcholine, or phosphatidylglycerol or salts thereof, or combinations thereof. In some embodiments, the phosphatidylcholine is dierucoyl phosphatidyl choline (DEPC). In some embodiments, the phosphatidylglycerol is dipalmitoyl phosphatidyl glycerol (DPPG) or a salt thereof (such as sodium DPPG). In some embodiments, the phosphatidylcholine is selected from DEPC, DSPC, DMPC, DOPC, or a combination thereof. In further embodiments, the neutral lipid comprises triglyceride, propylene glycol ester, ethylene glycol ester, or squalene, or combinations thereof. In some embodiments the neutral lipid comprises triglyceride. In some embodiments the triglyceride comprises triolein or tricaprylin, or a combination thereof. In some further embodiments, the multivesicular liposomes further comprise cholesterol and/or a plant sterol.

The concentrations of the amphipathic lipids, neutral lipids, and cholesterol present in the water-immiscible solvent used to make the MVLs typically range from 1-120 mM, 2-120 mM, and 10-120 mM, respectively. In some embodiments, the concentrations of the amphipathic lipids, neutral lipids, and cholesterol may range from about 20 mM to about 80 mM, about 8 mM to about 80 mM, and about 25 to about 80 mM, respectively. Specific examples of such concentrations are summarized in Example 1 and Table 3 herein. In some embodiments, the lipid components include DEPC, DPPG or a salt thereof (e.g., sodium DPPG), tricaprylin, and cholesterol. In further embodiments, the concentration of DEPC in the lipid solution can be from about 10 mM to about 40 mM, about 15 mM to about 35 mM, or about 16 mM to about 33 mM. The concentration of DPPG (or a salt thereof) in the lipid solution can be from about 4 mM to about 20 mM, from about 5.5 mM to about 18 mM, or from about 6.8 mM to about 14 mM. The concentration of tricaprylin in the lipid solution can be from about 20 mM to about 60 mM, or from about 24 mM to about 50 mM. The concentration of cholesterol in the lipid solution can be from about 20 mM to about 60 mM, or from about 24 mM to about 50 mM.

In any embodiments of the process described herein, dexamethasone or the ester or ester salt thereof is in the form of dexamethasone sodium phosphate.

In some embodiments, adjusting the concentration of certain lipid component(s) may have an impact on the sustained release rate of dexamethasone or DSP. While it is generally understood that when a higher concentration of the lipid component(s) are used in the manufacturing process of the MVLs, a slower release of the active agent may be observed, at least partially due to the improved strength of the lipid membrane of the MVL particles. However, high lipid concentrations may also have certain drawbacks, such as difficulty in handling of the lipid mixture due to increased stickiness and clogging of the pores of the filter during the filtration of the MVL particles. In some examples, the DSP-MVLs comprise DPPG. In some embodiments, decreasing the amount of DPPG in OBLT led to improved aggregation. Surprisingly, reducing the amount of DPPG to 8 mM in OBLT did not affect PK profile relative to the batch made with OBLT.

Many types of volatile organic solvents can be used in the present application, including ethers, esters, halogenated ethers, hydrocarbons, halohydrocarbons, or freon. For example, diethyl ether, chloroform, methylene chloride, tetrahydrofuran, ethyl acetate, and any combinations thereof are suitable for use in making the formulations. In some embodiments, methylene chloride is used. In some other embodiments, chloroform is used.

The lipid solution and first aqueous solution are mixed by mechanical turbulence, such as through use of rotating or vibrating blades, shaking, extrusion through baffled structures or porous pipes, or by ultrasound, or by the use of a three fluid nozzle (described in U.S. Pat. No. 9,737,482) to produce a water-in-oil emulsion. The water-in-oil emulsion can then be dispersed into a second aqueous solution by means described above, to form solvent-containing spherules suspended in the second aqueous solution, a water-in-oil-in-water emulsion is formed. The term "solvent-containing spherules" refers to a microscopic spheroid droplet containing organic solvent, within which are suspended multiple smaller droplets of aqueous solution.

The volatile organic solvent is then removed from the spherules by exposing to a pressurized stream of gas. For instance, such a pressurized stream of gas can cause surface evaporation from the second emulsion, sparging the second emulsion with a gas, or contacting the second emulsion with a gas in a spray chamber. When the solvent is substantially or completely evaporated, MVLs are formed. Gases which can be used for the evaporation include nitrogen, argon, helium, oxygen, hydrogen, and carbon dioxide, mixtures thereof, or clean compressed air. Alternately, the volatile solvent can be removed by sparging, rotary evaporation, diafiltration or with the use of solvent selective membranes, or contacting with a gas in a spray chamber.

As discussed above, dexamethasone or an ester or an ester salt thereof (such as DSP) can be incorporated in the MVLs by inclusion in the first aqueous solution. DSP can also be incorporated in the MVLs by inclusion in the lipid solution or both the lipid solution and first aqueous solution. Alternatively, dexamethasone or an ester or an ester salt thereof can also be incorporated in the lipid solution. The amount of DSP recovered in the instant MVLs was assayed by diluting the suspension of the DSP-MVL 50 fold into 100% methanol, then injecting the resulting mixture into an HPLC (Hewlett-Packard Model 1100 with C-18 column; running solvent system: 51% MeOH; 49% aqueous buffer containing monobasic sodium phosphate ($NaH_2PO_4$), $H_3PO_4$, TEA and sodium dodecyl sulfate ("SDS"); pH=2.5) as described in the United States Pharmacopeia 37 (USP 37) assay for organic impurities with some minor modification. In some embodiments, the percent DSP yield is from about 40% to about 90% of the starting DSP amount, more preferably from about 50% to about 90%, more preferably from about 60% to about 90%.

Standard preparation of multivesicular liposomes is illustrated in U.S. Pat. Nos. 5,766,627 and 6,132,766, each of which is incorporated by reference in its entirety. Alternatively, DSP can be remotely loaded to the blank MVL particles, which is described in U.S. Pat. No. 9,974,744.

Pharmaceutical Compositions

In some embodiments, the MVL formulations of the present application optionally include a pharmaceutically acceptable carrier. The term "pharmaceutically-acceptable carrier," as used herein, means one or more compatible solid or liquid filler diluents or encapsulating substances, which are suitable for administration to an organism (such as a mammal, e.g., human being) and does not abrogate the biological activity of the active ingredient(s). The term "compatible," as used herein, means that the components of the composition are capable of being commingled with the subject compound, and with each other, in a manner such that there is no interaction, which would substantially reduce the pharmaceutical efficacy of the composition under ordinary use situations. Pharmaceutically-acceptable carriers must, of course, be of sufficiently high purity and sufficiently low toxicity to render them suitable for administration preferably to an animal, preferably mammal being treated.

Some examples of substances, which can serve as pharmaceutically-acceptable carriers or components thereof, are sugars, such as lactose, glucose and sucrose; starches, such as corn starch and potato starch; cellulose and its derivatives, such as sodium carboxymethyl cellulose, ethyl cellulose, and methyl cellulose; malt; gelatin; talc; calcium sulfate; polyols such as propylene glycol, glycerine, sorbitol, mannitol, and polyethylene glycol; alginic acid; emulsifiers, such as the TWEENS; salts, such as sodium chloride; wetting agents, such sodium lauryl sulfate; coloring agents; flavoring agents; stabilizers; antioxidants; preservatives; pyrogen-free water; isotonic saline; and phosphate buffer solutions.

The choice of a pharmaceutically-acceptable carrier to be used in conjunction with the subject compound is basically determined by the way the compound is to be administered.

Effective injectable compositions containing these compounds may be in either suspension or solution form. In the solution form, DSP-MVLs may be diluted in a physiologically acceptable vehicle. Such vehicles comprise a suitable solvent, a tonicity agent such as sucrose or saline, preservatives such as benzyl alcohol, if needed, and buffers. Useful solvents include, for example, water and aqueous alcohols, glycols, and carbonate esters such as diethyl carbonate.

Injectable suspension compositions require a liquid suspending medium, with or without adjuvants, as a vehicle. The suspending medium can be, for example, aqueous solutions of sodium chloride, sucrose, polyvinylpyrrolidone, polyethylene glycol, or combinations of the above.

Suitable physiologically acceptable storage solution components are used to keep the compound suspended in suspension compositions. The storage solution components can be chosen from thickeners such as carboxymethylcellulose, polyvinylpyrrolidone, gelatin and the alginates. Many surfactants are also useful as suspending agents. The suspending medium could also contain lecithin, alkylphenol polyethylene oxide adducts, naphthalenesulfonates, alkylbenzenesulfonates, or the polyoxyethylene sorbitan esters. The DSP-MVL storage suspension solution can contain additional additive(s).

Many substances which affect the hydrophilicity, density, and surface tension of the liquid suspending medium can assist in making injectable suspensions in individual cases. For example, silicone antifoams, sorbitol, and sugars can be useful suspending agents.

In some embodiments, the pharmaceutical composition containing DSP-MVLs as described herein provides sustained release of DSP over 12 hours, over 24 hours, over 36 hours, over 48 hours, over 60 hours, over 72 hours, over 96 hours, over 120 hours, over 144 hours, over 168 hours, over 192 hours, over 240 hours, over 288 hours, over 336 hours, over 500 hours, or over 672 hours. In further embodiments, the pharmaceutical composition provides sustained release of DSP over at least 120 hours (5 days). In still embodiments, the pharmaceutical composition provides sustained release of DSP over at least 168 hours (7 days). In still embodiments, the pharmaceutical composition provides sustained release of DSP over at least 336 hours (14 days). In still further embodiments, the pharmaceutical composition provides sustained release of DSP over at least 672 hours (28 days). In further embodiments, the pharmaceutical composition provides sustained release of DSP between 3 days to 28 days, 5 to 28 days or 7 to 28 days.

In some embodiments, the pharmaceutical composition containing DSP-MVLs as described herein provides less than about 1%, 2%, 3%, 4%, 5%, 10%, 15%, 20%, 25%, or 30% release of DSP in the first 24 hours. In some further embodiments, the pharmaceutical composition containing DSP-MVLs as described herein provides less than about 1%, 2%, 3%, 4%, 5%, 10%, 15%, 20%, 25%, or 30% release of DSP in the first 48 hours. In some embodiments, the pharmaceutical composition containing DSP-MVLs as described herein provides less than about 5%, 10%, 15%, 20%, 25%, or 30% release of DSP in the first 72 hours. In some embodiments, the pharmaceutical composition containing DSP-MVLs as described herein provides less than about 30%, 35%, 40%, 45%, 50%, 55%, 60%, 65%, 70%, 75%, 80%, 85%, 90% or 95% release of DSP in the first 168 hours. In some such embodiments, the % release is measured by % total AUC or cumulative AUC of the DSP.

EXAMPLES

The following examples, including experiments and results achieved, are provided for illustrative purposes only and are not to be construed as limiting the present application.

Example 1: Preparation of DSP-MVL Formulations

DSP-MVL formulations were manufactured as follows: DSP was solubilized in a first aqueous solution containing phosphoric acid and sucrose. Next, the aqueous solution was emulsified with an organic dichloromethane (DCM) solution containing: DOPC, DEPC or DPPG, with tricaprylin and/or triolein, and cholesterol, resulting in a water-in-oil (W/O) emulsion. The W/O emulsion was then emulsified in a second aqueous solution containing lysine or histidine and dextrose to produce a water-in-oil-in-water (W/O/W) emulsion. The W/O/W emulsion was then diluted with a third aqueous solution containing lysine or histidine and sorbitol or dextrose. This was stirred at 23° C. under a nitrogen stream to remove the DCM via evaporation. The resulting particles were then diluted in saline, centrifuged, and the supernatant was replaced with saline+/− buffering agents (e.g., 20 mM sodium phosphate at pH's of 5.5-7.6). After washing, the particles were diluted in saline (0.9% NaCl) or other buffer solutions to yield a product with a ~50% packed particle volume.

Exemplary manufacturing conditions are summarized in Tables A1-A3 herein. Table A1 summarizes the manufacturing conditions of the First Aqueous Solution. Table A2 summarizes the manufacturing conditions of the Lipid Components. Table A3 summarizes the manufacturing conditions of the Second Aqueous Solution. The first emulsion mixing parameter for Formulations 47-49 was 9000 rpm for 10 minutes, and the second emulsion mixing parameter was 4000 rpm for 5 minutes. The first emulsion mixing parameter for Formulations 3AA, 5AA, 8AA, 11AA, and 14AA was 70 Hz for 20 minutes, and the second emulsion mixing parameter was 25 Hz for 2.5 minutes. Formulations 47-49 were made in bench scale, Formulations 3AA, 5AA, 8AA, 11AA, 14AA, and 18AA were made in 1 L scale, and Formulations 4B and 1C were made in 4 L scale.

The following abbreviations are used herein:
CFM is Chloroform;
DCM is Dichloromethane ($CH_2Cl_2$);
Lys is Lysine;
His is Histidine;
Suc is Sucrose;
Sorb is Sorbitol;
Dex is Dextrose;
Chol is Cholesterol;
PSD is particle size distribution;
Osm/D refers to Osmotic/Density Modifying Agent;
EXP is comprised of DEPC (1,2-dierucoyl-sn-glycero-3-phosphocholine, 19.8 mM, 17.78 mg/mL); DPPG (1,2-dipalmitoyl-sn-glycero-3-phospho-rac-(1-glycerol), 3.54 mM, 2.64 mg/mL); cholesterol (26.72 mM, 10.34 mg/mL); TC (tricaprylin, 9.17 mM, 4.32 mg/mL); and water (0.07%);
OBLT is comprised of DEPC (1,2-dierucoyl-sn-glycero-3-phosphocholine, 26.4 mM, 23.71 mg/mL); DPPG (1,2-dipalmitoyl-sn-glycero-3-phospho-rac-(1-glycerol), 11.2 mM, 8.34 mg/mL); cholesterol (40 mM, 15.48 mg/mL); TC (tricaprylin, 40 mM, 18.84 mg/mL); and water (0.39%);
OBLT+2% TO comprises all the components of OBLT and triolein (0.8 mM);
75% OBLT is comprised of DEPC (1,2-dierucoyl-sn-glycero-3-phosphocholine, 19.8 mM, 17.8 mg/mL); DPPG (1,2-dipalmitoyl-sn-glycero-3-phospho-rac-(1-glycerol), 8.4 mM, 6.3 mg/mL); cholesterol (30 mM, 11.6 mg/mL); TC (tricaprylin, 30 mM, 14.1 mg/mL); and water (0.29%);
Lipid Formulation 1 is comprised of DEPC (1,2-dierucoyl-sn-glycero-3-phosphocholine, 16.1 mM, 14.5 mg/mL); DPPG (1,2-dipalmitoyl-sn-glycero-3-phospho-rac-(1-glycerol), 6.8 mM, 5.1 mg/mL); cholesterol (24.4 mM, 9.4 mg/mL); TC (tricaprylin, 24.4 mM, 11.5 mg/mL); water (0.29%, 3.18 mg/mL); and dexamethasone sodium phosphate (7 mg/mL);
Lipid Formulation 2 is comprised of DEPC (1,2-dierucoyl-sn-glycero phosphocholine, 33.0 mM, 29.6 mg/mL); DPPG (1,2-dipalmitoyl-sn-glycero-3-phospho-rac-(1-glycerol), 14.0 mM, 10.4 mg/mL); cholesterol (50 mM, 19.3 mg/mL); TC (tricaprylin, 50 mM, 23.5 mg/mL); water (0.29%, 6.35 mg/mL); and dexamethasone sodium phosphate (7 mg/mL);
Total DSP concentration refers to the amount of encapsulated dexamethasone sodium phosphate in the multivesicular liposomes and the unencapsulated dexamethasone sodium phosphate in the liquid suspending medium;

Percent DSP Yield refers to the amount of DSP obtained in the final product particle suspension, as compared to the amount incorporated into either the first aqueous or lipid solutions;

Supernatant (Sup) DSP concentration is the measurement of unencapsulated DSP concentration in the saline solution used to store DSP-MVL particle suspensions. Prior to measurement, the saline solution was added to the final formulation suspension and allowed to equilibrate overnight;

% PPV means packed particle volumes, measured by spinning the suspensions down with a centrifuge and measuring the height of the particles in a lipocrit tube with a ruler;

% Free means the amount of unencapsulated DSP in the supernatant versus the total amount of DSP in the suspension.

TABLE A1

Summary of First Aqueous Solution

| # | [DSP] (mg/mL) | [DSP] (mM) | pH modifier | [pH agent] (mM) | Tonicity Agent | [Tonicity Agent] (mM) | pH | mOsm |
|---|---|---|---|---|---|---|---|---|
| 47 | 21.7 | 42 | $H_3PO_4$ | 8 | Suc | 181 | 6.49 | 306 |
| 48 | 20 | 39 | $H_3PO_4$ | 2.5 | Suc | 187 | 6.98 | 297 |
| 49 | 19.6 | 38 | $H_3PO_4$ | 0.7 | Suc | 187 | 7.44 | 296 |
| 3AA | 20 | 38.7 | $H_3PO_4$ | ~0.5 | Suc | 190 | 7.5 | 295 |
| 5AA | 20 | 38.7 | $H_3PO_4$ | ~0.5 | Suc | 190 | 7.5 | 295 |
| 8AA | 20 | 38.7 | $H_3PO_4$ | ~0.5 | Suc | 190 | 7.5 | 295 |
| 11AA | 20 | 38.7 | $H_3PO_4$ | ~0.6 | Suc | 190 | 7.53 | 295 |
| 14AA | 20 | 38.7 | $H_3PO_4$ | ~0.6 | Suc | 190 | 7.5 | 295 |
| 18AA | 20 | 38.7 | $H_3PO_4$ | ~0.6 | Suc | 190 | 7.5 | 295 |
| 4B | 20.1 | 38.9 | $H_3PO_4$ | ~0.6 | Suc | 180 | 7.5 | 289 |
| 1C | 37.3 | 72.2 | $H_3PO_4$ | ~0.6 | Suc | 75 | 7.5 | 243 |

TABLE A2

Summary of Lipid Components in the Starting Lipid Solution

| # | Base Lipid Solution | [DEPC] (mM) | [DPPG] (mM) | [Chol] (mM) | [TC] (mM) | [TO] (mM) | Solvent |
|---|---|---|---|---|---|---|---|
| 47 | OBLT | 26.4 | 11.2 | 40 | 40 | 0 | DCM |
| 48 | OBLT | 26.4 | 11.2 | 40 | 40 | 0 | DCM |
| 49 | OBLT | 26.4 | 11.2 | 40 | 40 | 0 | DCM |
| 3AA | OBLT | 26.4 | 11.2 | 40 | 40 | 0 | DCM |
| 5AA | OBLT + 2% TO | 26.4 | 11.2 | 40 | 40 | 0.8 | DCM |
| 8AA | 75% OBLT | 19.8 | 8.4 | 30 | 30 | 0 | DCM |
| 11AA | 75% OBLT (80% TC) | 19.8 | 8.4 | 30 | 24 | 0 | DCM |
| 14AA | 75% OBLT (60% TC) | 19.8 | 8.4 | 30 | 18 | 0 | DCM |
| 18AA | 75% OBLT | 19.8 | 8.4 | 30 | 24 | 0 | DCM |
| 4B | Lipid Formulation 1 | 16.1 | 6.8 | 24.4 | 24 | 0 | DCM |
| 1C | Lipid Formulation 2 | 33.0 | 14.0 | 50.0 | 50 | 0 | DCM |

TABLE A3

Summary of Second Aqueous Solution

| # | Tonicity Agent | [Tonicity Agent] (mM) | pH Agent | [pH agent] (mM) | pH | mOsm |
|---|---|---|---|---|---|---|
| 47 | Dex | 251 | Lys | 10 | 9.87 | 276 |
| 48 | Dex | 251 | Lys | 10 | 9.87 | 276 |
| 49 | Dex | 251 | Lys | 10 | 9.87 | 276 |
| 3AA | Dex | 163 | Lys | 10 | 9.9 | 170 |
| 5AA | Dex | 163 | Lys | 10 | 9.9 | 170 |
| 8AA | Dex | 163 | Lys | 10 | 9.9 | 170 |
| 11AA | Dex | 163 | Lys | 10 | 9.9 | 170 |
| 14AA | Dex | 163 | Lys | 10 | 9.9 | 170 |
| 18AA | Dex | 163 | Lys | 10 | 9.9 | 172 |
| 4B | Dex | 163 | Lys | 10 | 9.9 | 166 |
| 1C | Dex | 163 | Lys | 10 | 9.9 | 173 |

Example 2-Pharmacokinetic Studies of DSP-MVL Formulations in Rats and Beagles

Pharmacokinetic (PK) studies of the subcutaneous dosing of DSP discussed herein were performed on rats where bolus DSP was compared to various formulations of DSP-MVLs at doses between 1.0 to 3.5 mg/kg for rats and at 0.5 mg/kg for beagles. Formulations 3AA, 5AA, 8AA, 11AA, 14AA, 4B, and 1C were diluted to 19-20% PPV from the initial PPV of about 30-45% with a final DSP concentration of approximately about 3 mg/mL to 3.5 mg/mL. Formulations 47-49 were not diluted, and the DSP concentration in the final product was approximately 7 mg/mL. In addition, PK studies of Formulation 18AA were performed on beagles through subcutaneous and epidural dosing of DSP of about 0.5 mg/kg.

Plasma samples were collected at different times points (0, 24, 48, 72, 96, 120, 144 and 168 hours post dose) for analysis. Blood samples were collected via the right saphenous vein using a 19-gauge needle prick or cardiac puncture for the final time point, placed into chilled tubes containing the appropriate anticoagulant, inverted several times to mix, protected from light, and kept on ice until centrifugation. A summary of the data in FIG. 1-6 is set forth below in Tables 1-2. For the rat studies, Cumulative % AUC is expressed as a percentage of the total AUC obtained in animals administered with Free DSP. For the dog studies, Cumulative % AUC is expressed as a percentage of the total AUC for each dog.

FIG. 1 is a line chart illustrating the dose normalized dexamethasone plasma levels obtained in rats as a function of time, following administration of several DSP-MVL formulations varying in internal pH (Formulations 47-49) as compared to DSP in a saline solution ("Free DSP Solution" Formulation).

Figure 2:
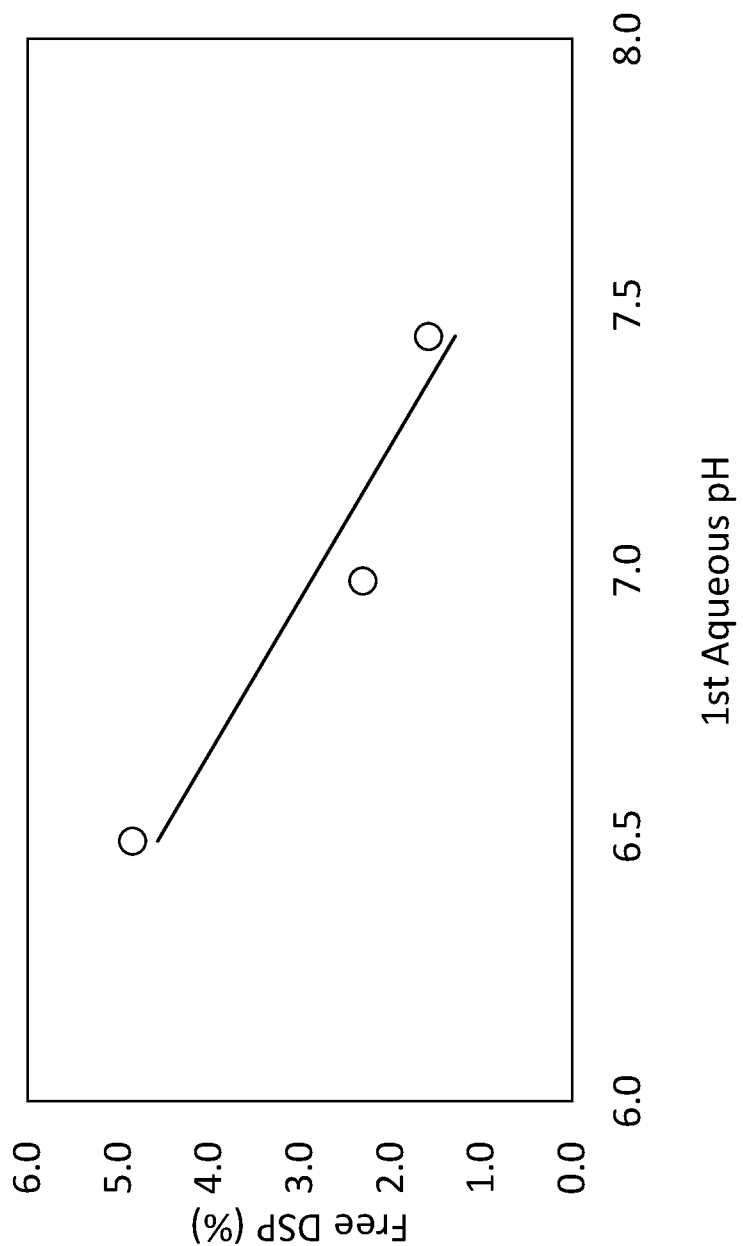
FIG. 2 is a line chart illustrating the percentage of free DSP in the DSP-MVLs composition as a function of the first aqueous solution pH.

FIG. 2 is a line chart illustrating the percentage of free or unencapsulated DSP outside the liposomal particles as a function of the first aqueous solution pH of several DSP-MVL formulations varying in internal pH (Formulations 47-49) in a stability testing experiment where the formulations are stored at 37° C. for 7 days.

Figure 3:
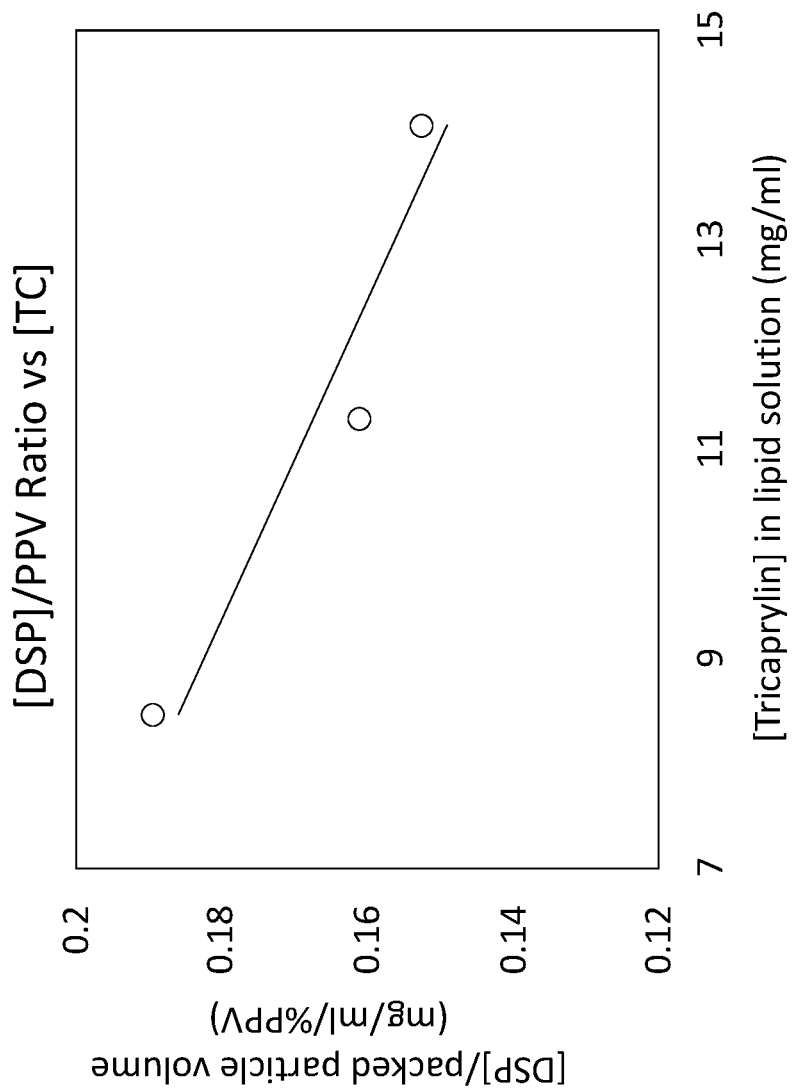
FIG. 3 is a line chart illustrating the ratio between DSP concentration to the percent packed particle volume (% PPV) as a function of tricaprylin concentration in the lipid solution.

FIG. 3 is a line chart illustrating the ratio between DSP concentration to the PPV as a function of tricaprylin concentration of several DSP-MVL formulations varying in tricaprylin concentration (Formulations 8AA, 11AA, and 14AA).

Figure 4:
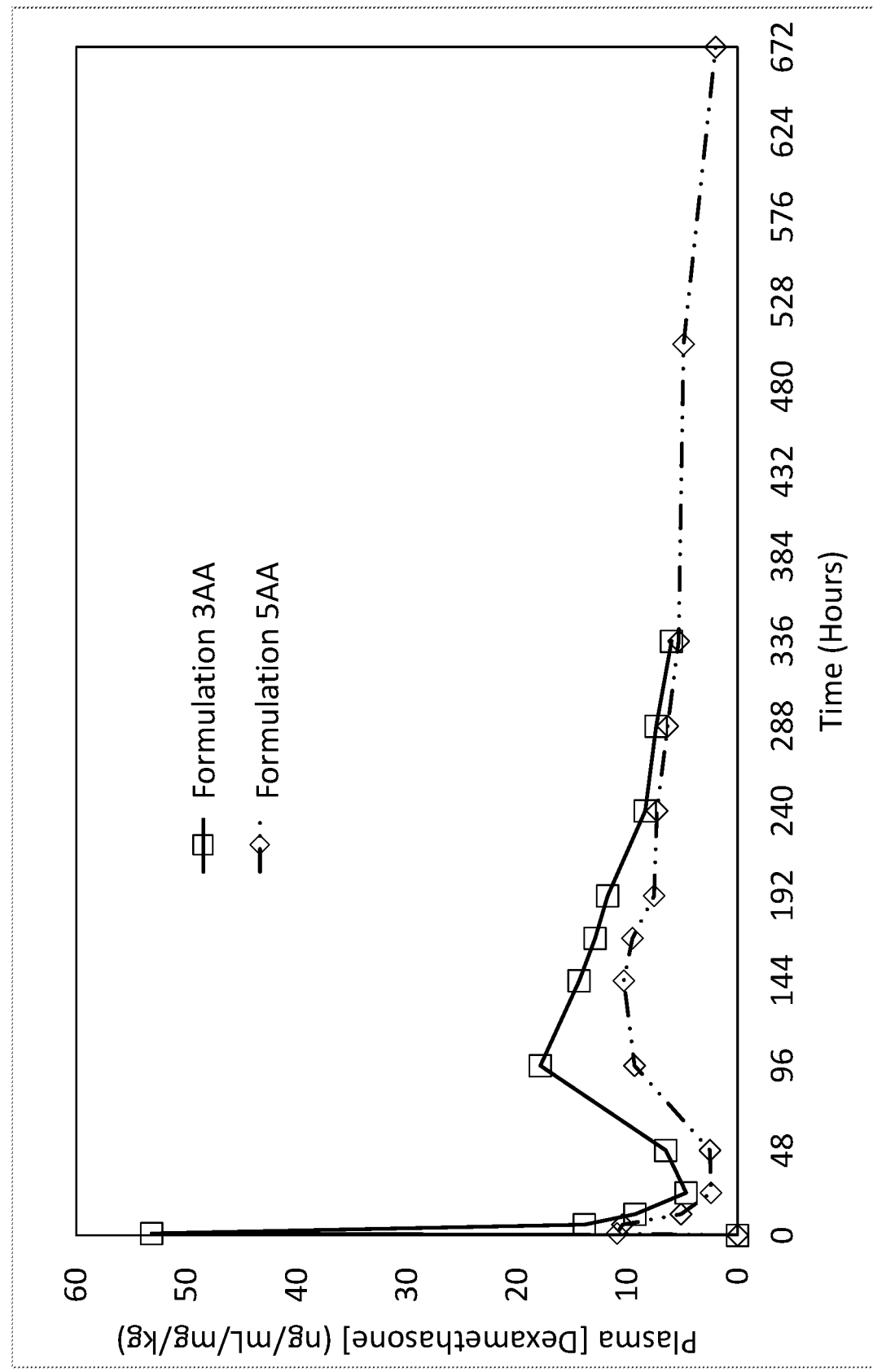
FIG. 4 is a line chart illustrating the dose normalized dexamethasone plasma level as a function of time, following a single injection of several DSP-MVL formulations with varying triolein concentrations.

FIG. 4 is a line chart illustrating the dose normalized dexamethasone plasma level obtained in rats as a function of time, following administration of two DSP-MVL formulations with and without triolein (Formulations 5AA and 3AA).

Figure 5:
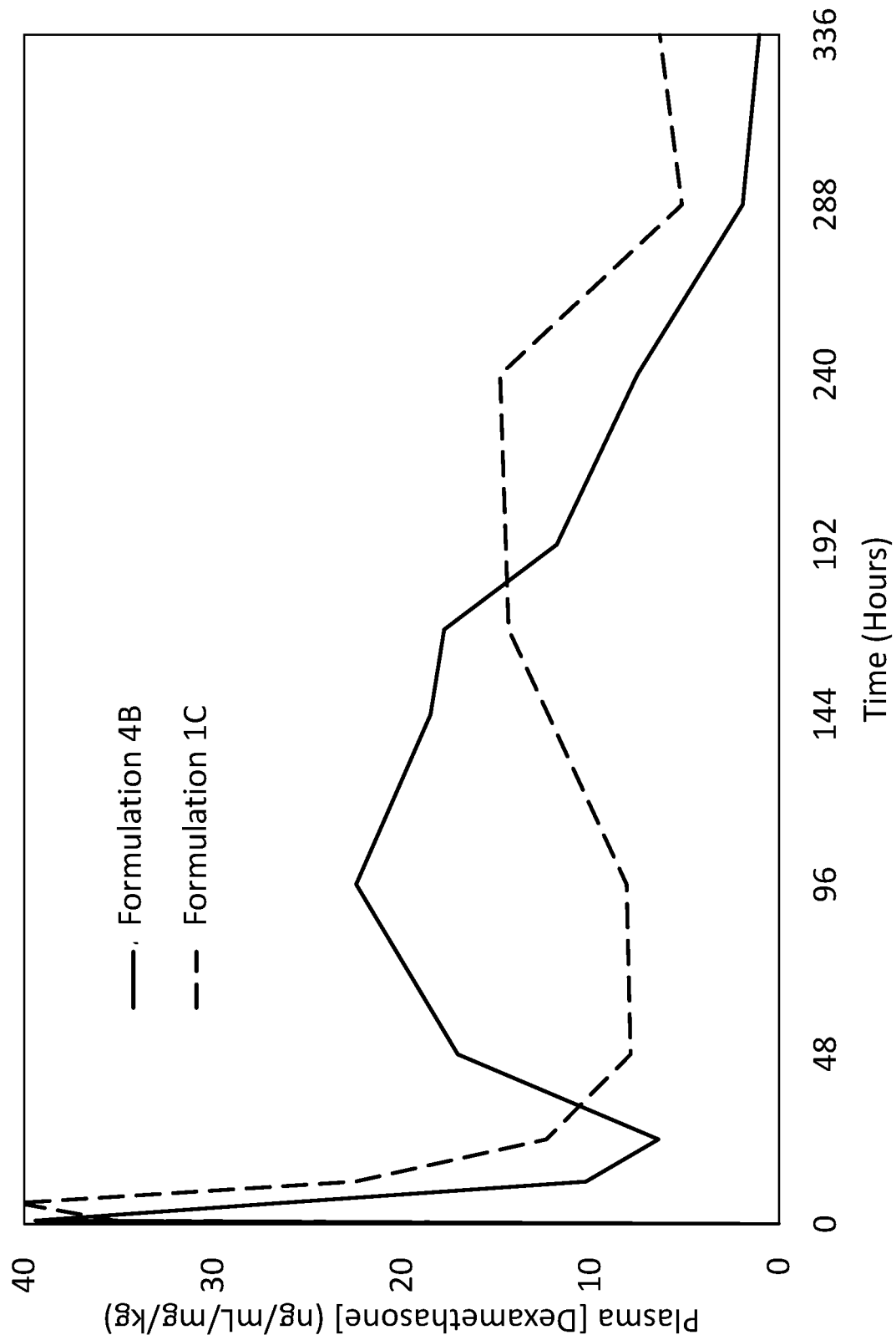
FIG. 5 is a line chart illustrating the dose normalized dexamethasone plasma levels obtained in rats as a function of time, following administration of several DSP-MVL formulations varying in lipid component concentrations.

FIG. 5 is a line chart illustrating the dose normalized dexamethasone plasma levels obtained in rats as a function of time, following administration of several DSP-MVL formulations varying in lipid component concentrations (Formulations 4B and 1C).

Figure 6:
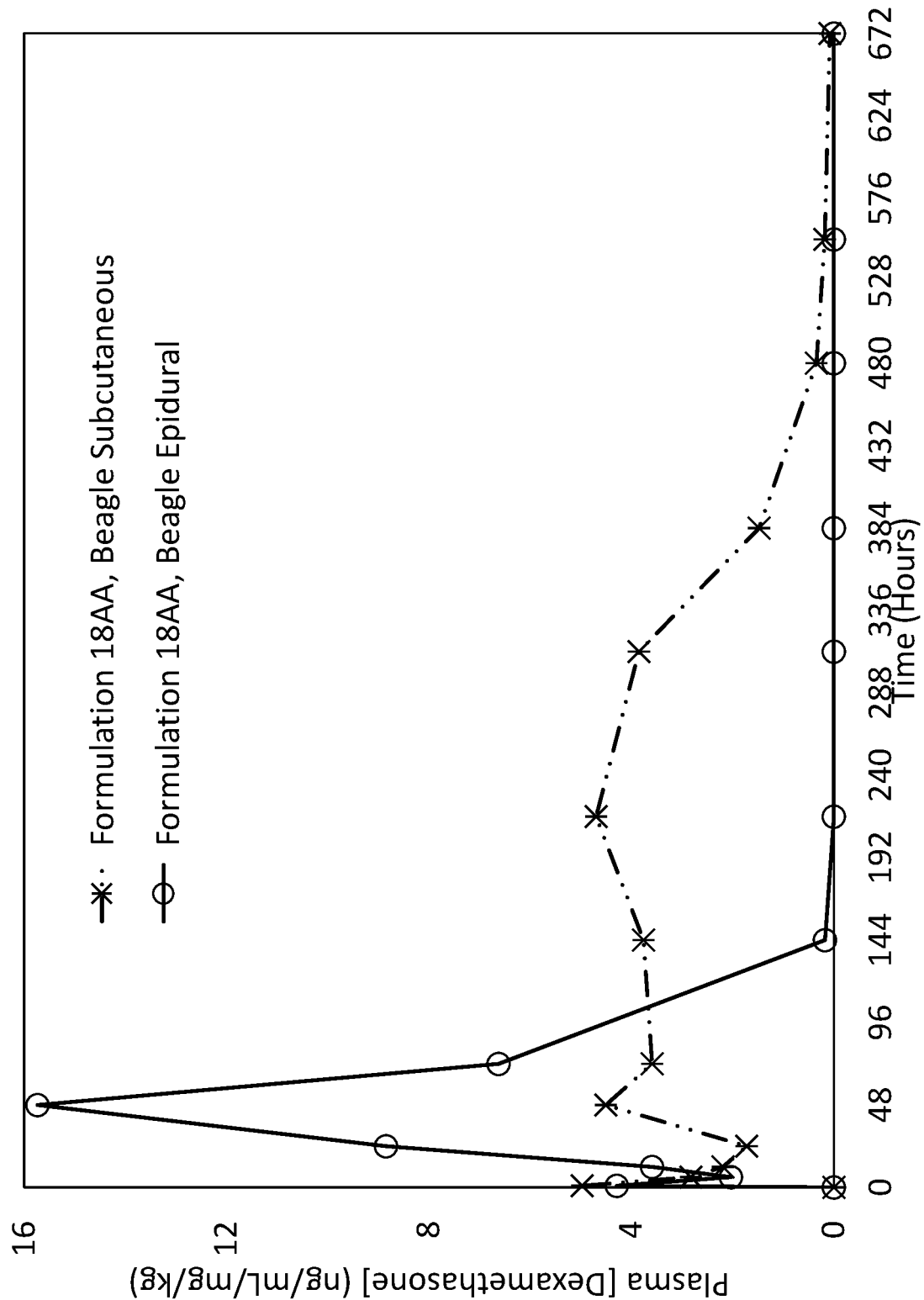
FIG. 6 is a line chart illustrating the dose normalized dexamethasone plasma levels obtained in beagles as a function of time, following administration of a DSP-MVL formulation via subcutaneous and epidural administration respectively.

FIG. 6 is a line chart illustrating the dose normalized dexamethasone plasma levels obtained in beagles as a function of time, following administration of DSP-MVL formulation (Formulation 18AA) via subcutaneous and epidural administration respectively.

It was observed that Formulation 1C utilizing 125% OBLT provided about 88% DSP-MVL yield and 30% PPV, while Formulation 4B utilizing 61% OBLT provided a 70% DSP-MVL yield and about 46% PPV. In addition, as illustrated in FIG. 5, Formula 4B had a $T_{max}$ of 1 hour, while Formulation 1C had a $T_{max}$ of 6 hours. Both formulations provided a $C_{max}$ of about 64-65 ng/mL.

TABLE 1

Summary of Select DSP-MVL Formulations

| Formulation | Total [DSP] (mg/mL) | % DSP Yield | Sup [DSP] (mg/mL) | Total [DSP] undiluted mg/mL (% PPV) | % PPV | % Free | Ext. pH | Int. pH | PSD (initial) d10 | d50 | d90 |
|---|---|---|---|---|---|---|---|---|---|---|---|
| Free DSP | 7.0 | N/A | N/A | N/A | N/A | N/A | N/A | N/A | N/A | N/A | N/A |
| 47 | 7.6 | 87 | 0.08 | N/A | 45 | 0.58 | 7.3 | 6.7 | 9 | 21 | 44 |
| 48 | 6.9 | 91 | 0.11 | N/A | 43 | 0.92 | 7.3 | 7.1 | 9 | 25 | 51 |
| 49 | 7.5 | 90 | 0.12 | N/A | 47 | 0.86 | 7.4 | 7.6 | 9 | 17 | 36 |
| 3AA | 3.3 | N/A | 0.06 | 6.86 (43.9) | 19 | 1.36 | 9.2 | 7.9 | 10 | 33 | 59 |
| 5AA | 3.31 | N/A | 0.06 | 6.69 (48.6) | 25 | 1.27 | 8.9 | 7.7 | 12 | 28 | 59 |
| 8AA | 2.83 | N/A | 0.05 | 6.37 (48.6) | 19 | 1.56 | 8.4 | 7.6 | 11 | 26 | 50 |
| 11AA | 3.12 | N/A | 0.08 | 6.74 (42) | 20 | 2.09 | 8.7 | N/A | 11 | 25 | 48 |
| 14AA | 3.17 | N/A | 0.08 | 8.33 (44) | 19 | 1.96 | 8.8 | N/A | 12 | 20 | 33 |
| 18AA | 7.4 | N/A | N/A | 7.4 (45) | 45 | 1.40 | 6.8 | N/A | 12 | 29 | 65 |
| 4B | 3.5 | 70 | 0.26 | 8.66 (46.4) | 20 | 1.30 | 7.0 | N/A | 9 | 33 | 57 |
| 1C | 3.5 | 87.9 | 0.31 | 10.46 (30) | 10 | 2.07 | 7.0 | N/A | 10 | 24 | 40 |

TABLE 2

Summary of PK Data for Select DSP-MVL Formulations

| Formulation | Species | Dose (mg/kg) | $C_{max}$ (ng/mL) | $C_{max}/C_{avg}$ | $T_{max}$ (hr) | AUC/dose(ng-hr/mL/mg/kg) | Cumulative AUC % at 7 days | Cumulative AUC % at 14 days |
|---|---|---|---|---|---|---|---|---|
| Free DSP | Rat | 3.2 | 2622.2 | 2.1 | 1 | 1182 | 100 | 100 |
| 47 | Rat | 3.5 | 128.5 | 3.2 | 48 | 685 | 63 | N/A |
| 48 | Rat | 3.2 | 92.3 | 2.7 | 144 | 635 | 53 | N/A |
| 49 | Rat | 3.5 | 45.0 | 1.6 | 144 | 382 | 35 | N/A |
| 3AA | Rat | 1.50 | 81 | 4 | 1 | 2429 | 57 | 95 |
| 5AA | Rat | 1.50 | 16.70 | 1.50 | 1 | 2429 | 32 | 62 |
| 8AA | Rat | 1.30 | 27.20 | 1.90 | 96 | 2803 | 69 | 107 |
| 11AA | Rat | 1.40 | 41.60 | 1.80 | 96 | 2603 | 107 | 134 |
| 14AA | Rat | 1.50 | 24.50 | 1.80 | 144 | 2429 | 46 | 90 |

TABLE 2-continued

Summary of PK Data for Select DSP-MVL Formulations

| Formulation | Species | Dose (mg/kg) | $C_{max}$ (ng/mL) | $C_{max}/C_{avg}$ | $T_{max}$ (hr) | AUC/dose(ng-hr/mL/mg/kg) | Cumulative AUC % at 7 days | Cumulative AUC % at 14 days |
|---|---|---|---|---|---|---|---|---|
| 18AA subcutaneous | Beagle | 0.5 | 2.4 | 1.17 | 1 | 3051.2 | 40 | 83 |
| 18AA epidural | Beagle | 0.5 | 8.1 | 1.52 | 48 | 1847 | 100 | 100 |
| 4B | Rat | 1.6 | 64 | 2.8 | 1 | 2271.875 | 80 | 95 |
| 1C | Rat | 1.6 | 65 | 2.7 | 6 | 1960 | 53 | 82 |

Example 3—Effects of Tricaprylin Concentration on Encapsulation Efficiency of DSP-MVL Formulations As depicted in FIG. 3, decreasing the tricaprylin concentration in the lipid solutions increased the encapsulation efficiency of DSP-MVL Formulations. For example, a tricaprylin concentration in the lipid solution of about 14 mg/mL resulted in an encapsulation efficiency of 0.13 ([DSP]/% PPV), while a tricaprylin concentration of about 8.5 mg/mL resulted in an encapsulation efficiency of 0.19 ([DSP]/% PPV). A summary of the data in FIG. 3 is set forth below in Table 3.

TABLE 3

Effects of Tricaprylin Concentration

| Formulation | Lipid Components | | | | | Encapsulation | |
|---|---|---|---|---|---|---|---|
| | [Chol] (mg/mL) | [DEPC] (mg/mL) | [DPPG] (mg/mL) | [TC] (mg/mL) | [DSP] (mg/mL) | % PPV | Efficiency ([DSP]/% PPV) |
| 8AA | 11.6 | 1.8 | 6.2 | 14.1 | 6.4 | 48.6 | 0.13 |
| 11AA | 11.6 | 1.8 | 6.2 | 11.3 | 6.8 | 42 | 0.16 |
| 14AA | 11.6 | 1.8 | 6.2 | 8.5 | 8.3 | 44 | 0.19 |

What is claimed is:

1. A composition of dexamethasone encapsulated multivesicular liposomes (MVLs), comprising:
   dexamethasone, an ester or an ester salt thereof, and at least one pH modifying agent encapsulated in a plurality of internal aqueous chambers of the MVLs separated by lipid membranes, wherein the lipid membranes comprise at least one amphipathic lipid, cholesterol, and at least one triglyceride; and
   an aqueous medium in which the dexamethasone encapsulated MVLs are suspended;
   wherein the pH of the internal aqueous chambers of the MVLs is from about 6.5 to about 7.6;
   wherein the dexamethasone or the ester or ester salt thereof is in the form of dexamethasone sodium phosphate,
   wherein the concentration of dexamethasone sodium phosphate in the composition is from about 2 mg/mL to about 10 mg/mL, and
   wherein the composition comprises less than 5% by weight of unencapsulated dexamethasone sodium phosphate of the total amount of dexamethasone sodium phosphate in the composition after storing at about 5° C. for at least 6 months.

2. The composition of claim 1, wherein the pH of the internal aqueous chambers of the MVLs is about 7.5.

3. The composition of claim 1, wherein the amphipathic lipid comprises a phosphatidylcholine or a salt thereof, a phosphatidylglycerol or a salt thereof, or combinations thereof.

4. The composition of claim 3, wherein the phosphatidylglycerol is DPPG or a salt thereof.

5. The composition of claim 3, wherein the phosphatidylcholine is selected from the group consisting of DEPC, DSPC, DMPC, DOPC, and salts and combinations thereof.

6. The composition of claim 1, wherein the lipid membranes comprise DPPG, DEPC, cholesterol and at least one triglyceride.

7. The composition of claim 6, wherein the triglyceride comprises triolein or tricaprylin, or a combination thereof, and wherein the percentage of the triglyceride in the lipid membrane is about 0.5% to about 30% by weight.

8. The composition of claim 1, wherein the concentration of dexamethasone sodium phosphate in the composition is about 7 mg/mL.

9. The composition of claim 1, wherein the aqueous medium in which the dexamethasone sodium phosphate encapsulated MVLs are suspended has a pH range from about 6.5 to about 7.5.

10. The composition of claim 9, wherein the pH of the aqueous medium is about 7.0.

11. The composition of claim 1, wherein the multivesicular liposomes have a $D_{50}$ particle size distribution from about 20 μm to about 40 μm.

12. The composition of claim 1, wherein the percent packed particle volume (% PPV) of the dexamethasone sodium phosphate encapsulated MVLs in the composition is from about 20% to about 45%.

13. The composition of claim 1, wherein a single administration of the composition provides a sustained release of dexamethasone sodium phosphate for about 14 days to about 28 days.

14. A method for treating or ameliorating pain or inflammation in a subject in need thereof, comprising administering a composition as in claim 1 to the subject.

15. The method of claim 14, wherein the administration is selected from the group consisting of subcutaneous injection, tissue injection, intramuscular injection, spinal injection, intraarticular injection, intraocular injection, epidural injection, intrathecal injection, intraocular injection, intraotic injection, and perineural injection, and combinations thereof.

16. The method of claim 15, wherein the administration is spinal injection, epidural injection, or intrathecal injection.

17. The method of claim 14, wherein a single administration provides a sustained release of dexamethasone sodium phosphate for about 14 days to about 28 days.

18. The composition of claim 1, wherein the pH modifying agent comprises phosphoric acid.

19. A composition of dexamethasone sodium phosphate encapsulated multivesicular liposomes (MVLs), comprising:
dexamethasone sodium phosphate and at least one pH modifying agent encapsulated in a plurality of internal aqueous chambers of the MVLs separated by lipid membranes,
wherein the lipid membranes comprise DEPC, DPPG, cholesterol, and at least one triglyceride,
wherein the triglyceride is selected from triolein and tricaprylin, or a combination thereof, and wherein the percentage of triglyceride in the lipid membrane is about 15% to about 30% by weight; and
an aqueous medium in which the dexamethasone sodium phosphate encapsulated MVLs are suspended;
wherein dexamethasone sodium phosphate encapsulated MVLs have an internal pH from about 6.5 to about 7.6,
the concentration of dexamethasone sodium phosphate in the composition is from about 3.5 mg/mL to about 8 mg/mL, and
the composition comprises less than 5% by weight of unencapsulated dexamethasone sodium phosphate of the total amount of dexamethasone sodium phosphate in the composition after storing at about 5° C. for at least 6 months.

20. The composition of claim 19, wherein the dexamethasone sodium phosphate encapsulated MVLs have an internal pH from about 7.1 to about 7.6.

21. The composition of claim 20, wherein the concentration of dexamethasone sodium phosphate in the composition is about 7 mg/mL.

22. A method for treating or ameliorating pain in a subject in need thereof, comprising administering a single epidural injection of the composition of claim 21 to the subject, wherein the administration provides a sustained release of dexamethasone sodium phosphate from about 14 days to about 28 days.

* * * * *